(12) United States Patent
Linschoten

(10) Patent No.: US 7,872,052 B2
(45) Date of Patent: Jan. 18, 2011

(54) USE OF HETEROCYCLIC COMPOUNDS AS SCCE INHIBITORS

(75) Inventor: Marcel Linschoten, Haninge (SE)

(73) Assignee: Arexis AB (SE)

( * ) Notice: Subject to any disclaimer, the term of this patent is extended or adjusted under 35 U.S.C. 154(b) by 270 days.

(21) Appl. No.: 10/559,322

(22) PCT Filed: Jun. 7, 2004

(86) PCT No.: PCT/DK2004/000388

§ 371 (c)(1),
(2), (4) Date: Apr. 26, 2006

(87) PCT Pub. No.: WO2004/108139

PCT Pub. Date: Dec. 16, 2004

(65) Prior Publication Data

US 2006/0258651 A1    Nov. 16, 2006

(30) Foreign Application Priority Data

| Jun. 6, 2003 | (DK) | 2003 00840 |
| Jun. 6, 2003 | (DK) | 2003 00842 |
| Jun. 6, 2003 | (DK) | 2003 00843 |
| Jun. 6, 2003 | (DK) | 2003 00844 |

(51) Int. Cl.
*A01N 27/00* (2006.01)
*A61K 31/54* (2006.01)
*A61K 9/00* (2006.01)

(52) U.S. Cl. ............ 514/766; 514/222.8; 424/400

(58) Field of Classification Search .......... None
See application file for complete search history.

(56) References Cited

U.S. PATENT DOCUMENTS 4,251,531 A * 2/1981 Doria et al. ......... 514/266.23
5,073,559 A * 12/1991 Coates ................. 514/263.3
5,346,886 A * 9/1994 Lezdey et al. ............. 514/8

OTHER PUBLICATIONS

Gilmore et al, Synthesis and Evaluation of 2-aryl-4H-3,1-benzoxazin-4-ones as Clr serine protease inhibitors, Bioorganic & Medicinal Chemistry Letters, 1996, 6(6), 679-682.*
http://www.merck.com/mmpe/sec10/ch116/ch116b.html (accessed Mar. 20, 2008).*
M. Mordarski, et al., "Antitumor properties of 1,3-oxazine derivatives. Derivatives of Dihydro-1,3-Oxazine Condensed with an Aromatic Ring in Position 5,6" *Archivum Immunologiae et Therapiae Experimentalis*, 1971, 19(4):533-545.
V. Pavlidis, et al., "The Synthesis of a Novel Series of Substituted 2-Phenyl-4H-3,1-benzoxazin-4-ones," *Synth. Commun.*, 1994, 24(4):533-548.
R. Law et al., "An Overview of the Serpin Superfamily," *Genome Biology*, 2006, 7:216-216;11.
D. Curiel et al., "Serum α1—Antitrypsin Deficiency Associated with the Common S-type (Glu$^{264}$→Val) Mutation Results from Intracellular Degradation of α1—Antitrypsin Prior to Secretion," The *Journal of Biological Chemistry*, 1989, vol. 264, No. 18, Issue of Jun. 25, 10477-10486.
Peter G. W. Gettins, "Serpin Structure, Mechanism, and Function," Chem. Rev., 2002, 102, 4751-4803.

* cited by examiner

*Primary Examiner*—Michael G Hartley
*Assistant Examiner*—Paul Dickinson
(74) *Attorney, Agent, or Firm*—Fish & Richardson P.C.

(57) ABSTRACT

The present invention relates to heterocyclic inhibitors of stratum corneum chymotryptic enzyme (SCCE). More particularly, the invention relates to the use of compounds with the formula (I) or (II) for treatment of certain diseases, in particular skin diseases such as pruritus, as well as cancer such as ovarian cancer.

24 Claims, 1 Drawing Sheet

USE OF HETEROCYCLIC COMPOUNDS AS SCCE INHIBITORS

CROSS REFERENCE TO RELATED APPLICATIONS

This application is a national phase filing under 35 U.S.C. §371 of international application number PCT/DK2004/000388, filed Jun. 7, 2004, which claims the benefit of priority of Danish application number PA 2003 00842, filed Jun. 6, 2003, Danish application number PA 2003 00843, filed Jun. 6, 2003, Danish application number PA 2003 00840, filed Jun. 6, 2003, and Danish application number PA 2003 00844, filed Jun. 6, 2003. The disclosures of the prior applications are considered part of (and are incorporated by reference in) the disclosure of this application.

FIELD OF THE INVENTION

The present invention relates to methods for inhibiting elevated serine protease stratum corneum chymotryptic enzyme (SCCE) activity. The invention further relates to the use of SCCE inhibitors of formula I and II for the treatment of diseases, more specifically for the treatment of skin diseases and ovarian cancer.

BACKGROUND OF THE INVENTION

Protein degrading enzymes have a wide spectrum of specificities and functions. Consequently they take part in numerous reactions, physiological as well as pathological, in cells and tissues. The possibility to design specific inhibitors makes proteases interesting targets for new drugs for treatment of diseases.

The serine protease stratum corneum chymotryptic enzyme (SCCE; EC 3.4.21.-; Swiss Prot P49862, also named kalllkrein 7; (WO 95/00651; Hansson L, et al T. Cloning, expression and characterization of stratum corneum chymotryptic enzyme. A skin-specific human serine proteinase; *J Biol Chem* 1994, 269:19420-19426; Yousef et al. The KLK7 (PRSS6) gene, encoding for the stratum corneum chymotryptic enzyme is a new member of the human kalllkrein gene family—genomic characterization, mapping, tissue expression and hormonal regulation. Gene 2000, 254: 119-128) is preferentially expressed in cornifying epithelia. Several studies have suggested that SCCE may take part in desquamation of cornified cells by means of degrading intercellular parts of desmosomes (Egelrud T. Desquamation in the stratum corneum. *Acta Derm Venereol* 2000, 208: 44-45). In stratum corneum extracts SCCE is responsible for a major part of the total proteolytic activity and is considered as having a potential role in skin pathophysiology, e.g. by acting as activators of precursors of pro-inflammatory cytokines (Nylander-Lundquist E, Egelrud T. Formation of active IL-1 beta from pro-IL-1 beta catalyzed by stratum corneum chymotryptic enzyme in vitro. *Acta Derm Venereol* 1997: 77: 203-206), or of protease activated cell surface receptors (Macfarlane S R, et al. Proteinase-activated receptors. *Pharmacol Rev* 2001, 53: 245-282).

Furthermore, SCCE has been observed to be up-regulated in psoriasis lesions (Ekholm E, Egelrud T. Stratum corneum chymotryptic enzyme in psoriasis. *Arch Dermatol Res* 1999, 291: 195-200) and in chronic lesions of atopic dermatitis (Hansson L, et al. Epidermal overexpression of stratum corneum chymotryptic enzyme in mice; a model for chronic itchy dermatitis. *J Invest Dermatol.* 2002, 118: 444-449). Together these results show that there is a disturbance in the keratinocyte expression of SCCE in two diseases characterized by chronic inflammation, epidermal hyperproliferation, and scaling. Increased activity of SCCE present in the skin may indeed play a significant part in skin pathophysiology and the use of inhibitors of SCCE activity presents a new therapeutically principle for the treatment of skin diseases.

Transgenic mice over-expressing human scce mRNA under a viral promoter have been generated (WO 02/062135.) The only phenotypic changes observed were found in the skin, which showed several histological changes similar to those seen in chronic inflammatory skin diseases in humans. The transgenic mice expressed human SCCE in suprabasal epidermal keratinocytes, and were found to develop pathological skin changes including increased epidermal thickness, hyperkeratosis, and a dermal infiltrate consisting of macrophages and granulocytes. There was also disturbed keratinocyte differentiation, epidermal hyperproliferation, increased transepidermal water loss and an induction of MHC II expression by keratinocytes. Furthermore, with increasing age the majority of the transgenic animals showed signs of severe itch (Hansson L, et al. Epidermal overexpression of stratum corneum chymotryptic enzyme in mice; a model for chronic itchy dermatitis. *J Invest Dermatol.* 2002, 118: 444-449; Ny A, Egelrud T. Transgenic mice overexpressing a serine protease in the skin: Evidence of Interferon γ-independent MHC II expression by Epidermal Keratinocytes. *Acta Derm Venereol.* 2003, 83:323-327; Ny A, Egelrud T Epidermal hyperproliferation precedes decreased skin barrier function In mice overexpressing stratum corneum chymotryptic enzyme. *Acta Derm Venereol.* 2004, 84:18-22). These transgenic mice will provide a useful animal model for human skin disease for the development of new treatment strategies and in the evaluation of therapeutically useful inhibitors of SCCE.

SCCE has also been found to be highly over-expressed in ovarian cancer (Tanimoto H, et al. The stratum corneum chymotryptic enzyme that mediates shedding and desquamation of skin cells is highly overexpressed in ovarian tumour cells. *Cancer* 1999, 86:2074-82, Kyriakopoulou L G, et al. Prognostic value of quantitatively assessed KLK7 expression in ovarian cancer. *Clin Biochem* 2003, 36:135-43). Inhibition of SCCE activity is therefore considered as a new therapeutical principle for the treatment of ovarian cancer.

SUMMARY OF THE INVENTION

It has now been found that the activity of SCCE can be inhibited by compounds with formula I or II. Furthermore, it has been found that such compounds are effective, in particular when topically applied, in reducing skin diseases, such as inflammatory skin diseases.

Accordingly, in a first aspect the invention relates to the use of a compound with the formula I or II

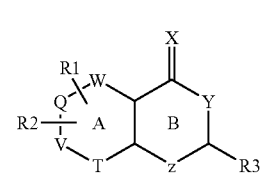

I

-continued

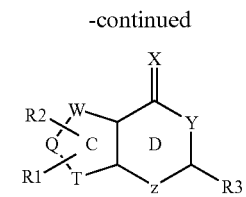

II wherein

X is O or S; Y is independently O, S, NH or N if the nitrogen atom is bonded to an adjacent carbon atom via a double bond; Z is independently O, NH or N if the nitrogen atom is bonded to an adjacent carbon atom via a double bond;

W, Q, V, and T are independently CH, $CH_2$, S, N, or O;

ring A, ring B, ring C and ring D may be aromatic, saturated or partly saturated;

$R_1$ and $R_2$, if present, are independently $C_{1-8}$-alkyl, $C_{2-8}$-alkenyl, $C_{2-8}$-alkynyl or $C_{3-6}$-cycloalkyl, each optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; H, halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, or tetrazole;

or $R_1$ and $R_2$, when bonded to adjacent atoms in ring A or ring C, together form a moiety $-(CH_2)_n-$, where n=1-5, and wherein 1, 2 or 3 $CH_2$ units in said moiety are optionally replaced by 1, 2 or 3 heteroatoms, wherein each heteroatom is individually selected from the group consisting of O, S, NH and N if the nitrogen atom is bonded to an adjacent atom via a double bond, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$ alkoxy, trifluoromethoxy, carbamoyl, $CONHR_4$, or $CON(R_4)_2$;

$R_3$ is aryl or heteroaryl, each optionally substituted with one or more halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, tetrazole, $C_{1-8}$-alkyl, $C_{2-8}$-alkenyl, $C_{2-8}$-alkynyl or $C_{3-6}$-cycloalkyl, each $C_{1-8}$-alkyl, $C_{2-8}$-alkenyl, $C_{2-8}$-alkynyl or $C_{3-6}$-cycloalkyl being optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl; and $R_4$ is $C_{1-4}$-alkyl, $C_{2-4}$-alkenyl, $C_{2-4}$-alkynyl, $C_{3-6}$-cycloalkyl, $C_{1-6}$-alkoxy, $C_{1-6}$-alkylthio, aryl, aryloxy, heteroaryl, or heteroaryloxy;

or a pharmaceutical acceptable salt thereof, for the manufacture of a medicament for the treatment or prevention of skin diseases.

In another aspect the invention relates to the use of a compound with the formula I or II, or a pharmaceutically acceptable salt thereof, for the manufacture of a medicament for the treatment of cancer.

In still another aspect the invention relates to a method for modulating and/or normalizing an impaired skin barrier in a mammal, which method comprises administering an effective amount of at least one compound with formula I or II, or a pharmaceutically acceptable salt thereof, to a mammal in need thereof.

In a further aspect the invention relates to a method for treatment of a skin disease which method comprises administering an effective amount of at least one compound with formula I or II, or a pharmaceutically acceptable salt thereof, to a mammal in need thereof.

In a still further aspect the invention relates to a method for treatment of mammals suffering from cancer, which method comprises administering an effective amount of at least one compound with formula I or II, or a pharmaceutically acceptable salt thereof, to a mammal in need thereof.

In an even further aspect the invention relates to a cosmetic or skin care composition comprising at least one compound with the formula I or II, or a pharmaceutically acceptable salt thereof, said composition being in a form suitable for topical administration, and selected from the group consisting of a cream, an ointment, a lotion, a liniment, a gel, a paste, a stick, a spray, a shampoo, a soap, a hair conditioner and a powder.

In yet another aspect the invention relates to the use of a compound with the formula I or II, or a pharmaceutically acceptable salt thereof, for treatment or prophylaxis of cosmetic skin conditions.

Other aspects of the present invention will be apparent from the below disclosure and the appended claims.

DETAILED DESCRIPTION OF THE INVENTION

Definitions

Figure 1:
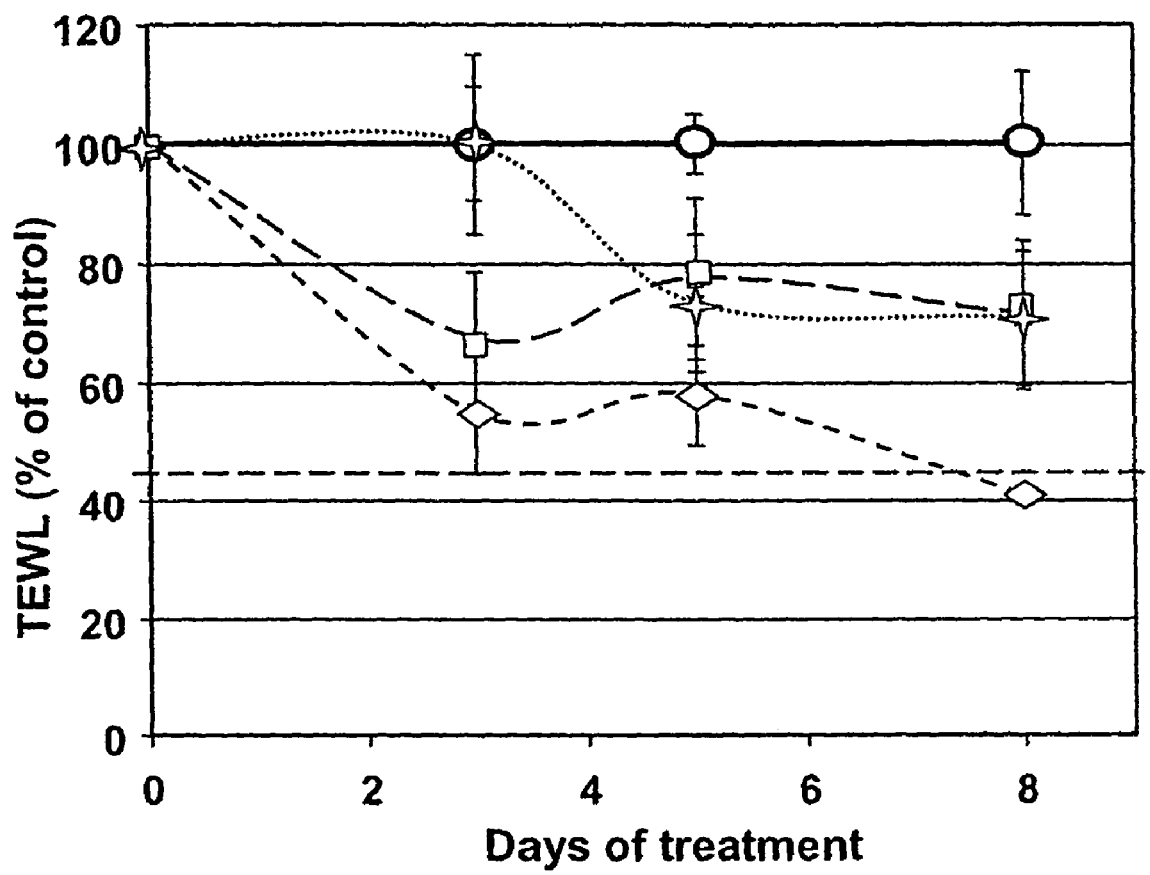
FIG. 1 shows the effect on transepidermal water loss (TEWL) in transgenic SCCE mice of a topically applied SCCE inhibitor, compound I-3 (2-(2-Iodo-phenyl)-6,7-dimethoxy-benzo[d][1,3]oxazin-4-one). □=30 μM inhibitor, ✦=300 μM inhibitor, ○=control (vehicle), ◇=betamethasone, ----=normal TEWL level in wild-type mice.

In the present context, the term "$C_{1-8}$-alkyl" is intended to mean a linear or branched saturated hydrocarbon chain wherein the chain has from one to eight carbon atoms, such as methyl, ethyl, n-propyl, isopropyl, n-butyl, isobutyl, sec-butyl, tert-butyl, pentyl, isopentyl, neopentyl, hexyl, heptyl and octyl. A branched hydrocarbon chain is intended to mean a $C_{1-8}$-alkyl substituted at any carbon with a hydrocarbon chain.

In the present context, the term "$C_{2-8}$-alkenyl" is intended to mean a linear or branched hydrocarbon chain having from two to eight carbon atoms and containing one or more double bonds. Illustrative examples of $C_{2-8}$-alkenyl groups include allyl, homo-allyl, vinyl, crotyl, butenyl, pentenyl, hexenyl, heptenyl and octenyl. Illustrative examples of $C_{2-8}$-alkenyl groups with more than one double bond include butadienyl, pentadienyl, hexadienyl, heptadienyl, hexatrienyl, heptatrienyl and octatrienyl groups as well as branched forms of these. The position of the double bond(s) may be at any position along the carbon chain.

In the present context, the term "$C_{2-8}$-alkynyl" is intended to mean a linear or branched hydrocarbon chain containing from two to eight carbon atoms and containing one or more triple bonds. Illustrative examples of $C_{2-8}$-alkynyl groups include acetylene, propynyl, butynyl, pentynyl, hexynyl, heptynyl and octynyl groups as well as branched forms of these. More than one bond may be unsaturated such that the "$C_{2-8}$-alkynyl" is a di-yne or enedi-yne as is known to the person skilled in the art. The position of the triple bond(s) may be at any position along the carbon chain.

In the present context the term "$C_{3-6}$-cycloalkyl" is intended to cover three-, four-, five- and six-membered rings comprising carbon atoms, wherein all carbon-carbon bonds are saturated. Specific examples include cyclopropyl, cyclobutyl, cyclopentyl and cyclohexyl.

When used herein the term "$C_{1-6}$-alkoxy" is intended to mean $C_{1-6}$-alkyl-oxy, such as methoxy, ethoxy, n-propoxy, isopropoxy, n-butoxy, isobutoxy, sec-butoxy, tert-butoxy, pentoxy, isopentoxy, neopentoxy and hexoxy.

The term "$C_{1-6}$-alkylthio" as used herein, refers to straight or branched $C_{1-6}$-alkyl wherein a carbon atom is covalently linked to a sulphur atom.

When used herein the term "halogen" refers to fluorine, chlorine, bromine, and iodine.

In the present context the term "aryl" is intended to mean a carbocyclic aromatic ring or ring system. Moreover, the term "aryl" includes fused ring systems wherein at least two aryl rings share a chemical bond. In the present context, the term "heteroaryl" is intended to mean an aryl group where one or more carbon atoms in an aromatic ring have been replaced with one or more heteroatoms, such as nitrogen, sulphur, phosphor or oxygen. Furthermore, in the present context, the term "heteroaryl" comprises fused ring systems wherein at least one aryl ring and at least one heteroaryl ring or at least two heteroaryls, share a chemical bond.

Specific examples of "aryl" and "heteroaryl" include optionally substituted phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, quinazolin, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1 2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydrobenzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimiclazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, and 10,11-dihydro-5H-dibenz[b,f]azepine-5-yl).

The term "leaving group" includes, but is not limited to, halogen, sulphonate or an acyl group. Other suitable leaving groups will be apparent to the person skilled in the art.

The term "protection group" (PG) refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagent compatible with the other functional group(s) generated in such protected reactions. Protection groups include but are not limited to $CH_3$, benzyl (Bn), butyloxycarbonyl (BOC), benzyloxycarbonyl (CBz), 9-fluorenylmethoxycarbonyl (Fmoc), or tosyl (Ts) groups. A person skilled in the art will know other nitrogen protection groups. Examples of protecting groups can be found in, for example, Greene et al. (1991) Protective Groups in Organic Chemistry, 2" Ed. (John Wiley & Sons, Inc., New York).

"Coupling agent" means an agent suitable for formation of acid derivatives from acids or activated acids and amines, phenols, alcohols, or acids including, but not limited to hydroxybenzotriazole (HOBt) and derivatives thereof and carbodiimides like dicyclohexylcarbodiimide and ethyldimethylaminopropyl carbodiimide (DCC, EIDAC). The skilled person will know suitable coupling agents. Activated acids include, but are not limited to acid chlorides, acid anhydrides, esters, and similar derivatives.

"Agent capable of introducing ring closure" means an agent capable of introducing combined hydrolysis and ring closure under absorption of water. This include, but are not limited to, organic and inorganic acid anhydrides, e.g. acetic anhydride and $P_2O_5$, mineral acids, e.g. concentrated sulfuric acid, phosphoric acid and the like, acid chlorides, e.g. $SOCl_2$, $PCl_5$, and $POCl_3$.

"Optional" or "optionally" means that the subsequently described event or circumstances may or may not occur, and that the description includes instances where said event or circumstance occur and instances in which is does not. For example, "aryl . . . optionally substituted" means that the aryl may or may not be substituted and that the description includes both unsubstituted aryls and aryls wherein substitution takes place.

"Treatment" means the administration of a therapeutically effective amount of a compound disclosed herein with the purpose of preventing any symptoms or disease state to develop, or with the purpose of curing or easing such symptoms or disease states already developed. The term "treatment" is thus meant to include prophylactic treatment.

The abbreviation "SCCE" refers in the present context to Stratum corneum chymotryptic enzyme Certain of the above defined terms may occur more than once in the above formulas I and II, and upon such occurrence each term shall be defined independently of the other.

The compounds of the present invention may have one or more asymmetric centres and it is intended that stereoisomers (optical isomers), as separated, pure or partially purified stereoisomers or racemic mixtures thereof are included within the scope of the invention.

As will be understood, the compounds of formula I or II described-herein are effective SCCE inhibitors. However, as some variation in the inhibition efficiency between the individual compounds of formula I or II may be present, the inventors have provided suitable preliminary assays which can be used in order to assess the inhibition efficiency of the compounds of formula I or II. For example, the "SCCE Inhibitor Test" described in Example 1 herein is a simple test which may be performed to initially assess the potency of the compound. Accordingly, a compound of formula I or II which is preferred for the methods and uses disclosed herein, is a compound which, when assayed in the "SCCE Inhibitor Test" described herein, has an $IC_{50}$ value of less than 5 μM. More preferably, the compound has an $IC_{50}$ value of less than 4 μM; even more preferably the compound has an $IC_{50}$ value of less than 3 μM, still more preferably the compound has an $IC_{50}$ value of less than 2 μM, most preferably the compound has an $IC_{50}$ value of less than 1 μM, such as an $IC_{50}$ value of less than 0.5 μM, when assayed in the "SCCE Inhibitor Test" described herein.

Alternatively, a compound of formula I or II which is preferred for the methods and uses disclosed herein, is a compound wherein the ratio between the $IC_{50}$ value of said compound and the $IC_{50}$ value of 2-phenyl-benzo[d][1,3]oxazin-4-one is less than 2.5, when assayed in the "SCCE Inhibitor Test" described herein. More preferably, the ratio is less than 2.0, even more preferably the ratio is less than 1.5, still more preferably the ratio is less than 1.0, most preferably the ratio is less than 0.5, such as less than 0.25, when assayed in the "SCCE Inhibitor Test" described herein The Ring Systems The formulas I and II include, but are not limited to, ring systems of the following types (all having substituents $R_1$, $R_2$ and $R_3$ placed as shown in formulas I and II and defined as above and in claim 1):

benzo[d][1,3]oxazin-4-one,
benzo[e][1,3]oxazin-4-one,
benzo[d][1,3]oxazin-4-thione,
3H-quinazolin-4-ones,
3H-quinazolin-4-thione,
benzo[d][1,3]thiazin-4-one,
thieno[3,2-d][1,3]oxazin-4-one,
thieno[2,3-d][1,3]oxazin-4-one,
thieno[3,2-e][1,3]oxazin-4-one,
thieno[2,3-e][1,3]oxazin-4-one,
thieno[3,2-d][1,3]oxazin-4-thione,
thieno[2,3-d][1,3]oxazin-4-thione,
3H-thieno[3,2-d]pyrimidine-4-thione,
3H-thieno[2,3-d]pyrimidine-4-thione,
3H-thieno[3,2-d]pyrimidine-4-one,
3H-thieno[2,3-d]pyrimidine-4-one,
1,6-dithia-4-aza-inden-7-one,
thieno[2,3-d][1,3]thiazin-4-one,
pyrido[2,3-d][1,3]oxazin-4-one,
pyrazino[2,3-d][1,3]oxazin-4-one,
pyrimido[4,5-d][1,3]oxazin-4-one,
pyrazolo[1,3]oxazin-4-one,
imidazo[1,3]oxazin-4-one,
piperidino[1,3]oxazin-4-one,
piperazino[1,3]oxazin-4-one,
morpholino[1,3]oxazin-4-one,
pyrrolidino[1,3]oxazin-4-one,
pyrrolino[1,3]oxazin-4-one,
imidazolino[1,3]oxazin-4-one,
pyrazolidino[1,3]oxazin-4-one,
pyrano[1,3]oxazin-4-one,
pyridino[1,3]oxazin-4-one,
pyridazino[1,3]oxazin-4-one,
pyrimidino[1,3]oxazin-4-one,
pyrazino[1,3]oxazin-4-one,
furano[1,3]oxazin-4-one,
pyrrolo[1,3]oxazin-4-one,
isoxazolo[1,3]oxazin-4-one,
isothiazolo[1,3]oxazin-4-one,
furazano[1,3]oxazin-4-one,
tetrahydrofurano[1,3]oxazin-4-one,
tetrahydrothiopheno[1,3]oxazin-4-one,
imidazolidino[1,3]oxazin-4-one,
pyrazolino[1,3]oxazin-4-one,
oxathiolano[1,3]oxazin-4-one,
oxazolo[1,3]oxazin-4-one,
isothiazolidino[1,3]oxazin-4-one,
thiazolidino[1,3]oxazin-4-one,
thiazolo[1,3]oxazin-4-one,
oxadiazolo[1,3]oxazin-4-one,
thiadiazolo[1,3]oxazin-4-one,
5,6,7,8-tetrahydro-3-oxa-9-thia-1-aza-fluoren-4-one,
5,6,7,8-tetrahydro-1-oxa-9-thia-3-aza-fluorene-4-one,
5,6,7,8-tetrahydro-3-oxa-9-thia-1-aza-fluorene-4-thione,
5,6,7,8-tetrahydro-3,9-dioxa-1-aza-fluoren-4-one,
5,6,7,8-tetrahydro-3-oxa-9-aza-1-aza-fluoren-4-one,
5,6,7,8-tetrahydro-3H-benzo[4,5]thieno[2,3-d]pyrimidine-4-thione,
5,6,7,8-tetrahydro-3H-benzo[4,5]thieno[2,3-d]pyrimidine-4-one,
5,6,7,8-tetrahydro-3,9-dithia-1-aza-fluoren-4-one,
2,3-dihydro-1H-5-oxa-8-thia-7-aza-cyclopenta[a]indene-4-one,
2,3-dihydro-1H-7-oxa-8-thia-5-aza-cyclopenta[a]indene-4-one,
2,3-dihydro-1H-5-oxa-8-thia-7-aza-cyclopenta[a]indene-4-thione,
1,2,3,5-tetrahydro-8-thia-5,7-diaza-cyclopenta[a]indene-4-thione,
1,2,3,5-tetrahydro-8-thia-5,7-diaza-cyclopenta[a]indene-4-one,
2,3-dihydro-1H-5,8-dithia-7-aza-cyclopenta[a]indene-4-one,
2,3-dihydro-1H-5,8-dioxa-7-aza-cyclopenta[a]indene-4-one,
1,2,3,8-tetrahydro-5-oxa-7,8-diaza-cyclopenta[a]indene-4-one,
6,7,8,9-tetrahydro-5H-3-oxa-10-thia-1-aza-benzo[a]azulen-4-one,
6,7,8,9-tetrahydro-5H-1-oxa-10-thia-3-aza-benzo[a]azulen-4-tone,
6,7,8,9-tetrahydro-5H-3-oxa-10-thia-1-aza-benzo[a]azulen-4-thione,
3,5,6,7,8,9-hexahydro-10-thia-1,3-diaza-benzo[a]azulen-4-one,
3,5,6,7,8,9-hexahydro-10-thia-1,3-diaza-benzo[a]azulen-4-one,
6,7,8,9-tetrahydro-5H-3,10-dithia-1-aza-benzo[a]azulen-4-one,
6,7,8,9-tetrahydro-5H-3,10-dioxa-1-aza-benzo[a]azulen-4-one or
5,6,7,8,9,10-hexahydro-3-oxa-1,10-dithia-benzo[a]azulen-4-one.

In a preferred embodiment of the invention ring A does not contain any heteroatoms and ring C contains at least one sulphur atom. Thus, in preferred embodiment of the invention the compounds are of the general formula Ia or IIa

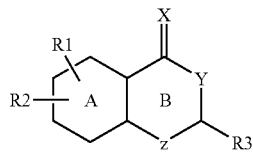

Ia

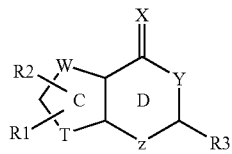

IIa wherein

X is O or S; Y is independently O, S, NH or N if the nitrogen atom is bonded to an adjacent carbon atom via a double bond; Z is independently O, NH or N if the nitrogen atom is bonded to an adjacent carbon atom via a double bond; T and W are CH, CH$_2$, or S, wherein one of T and W is S; and ring A, ring B, ring C and ring D may be aromatic, saturated or partly saturated.

More preferably, none of X, Y and Z are sulphur, i.e. referring to formula Ia and IIa above, X is O; Y is independently O, NH or N if the nitrogen atom is bonded to an adjacent carbon atom via a double bond; Z is independently O, NH or N if the nitrogen atom is bonded to an adjacent carbon atom via a double bond; T and W are CH, CH$_2$, or S, wherein one of T and W is S. In an even more preferred embodiment, ring B and D do not contain two nitrogen atoms. In a still more preferred embodiment, ring A and C are aromatic and ring B and D are partly saturated.

Accordingly, preferred examples of compounds having formula Ia or IIa include (R$_1$, R$_2$, R$_3$ as defined above):

benzo[d][1,3]oxazin-4-ones with the formula

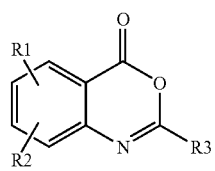

benzo[e][1,3]oxazin-4-ones with the formula

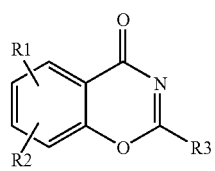

thieno[3,2-d][1,3]oxazin-4-ones with the formula

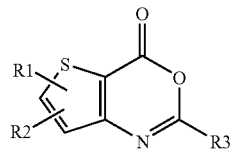

thieno[2,3-d][1,3]oxazin-4-ones with the formula

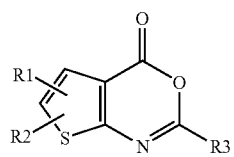

thieno[2,3-e][1,3]oxazin-4-ones with the formula (structure)

thieno[3,2-e][1,3]oxazin-4-ones with the formula (structure)

Isothiazolo[5,4-d][1,3]oxazin-4-ones with the formula

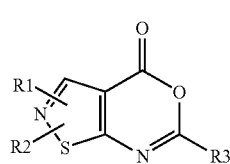

pyrido[3,4-d][1,3]oxazin-4-ones with the formula

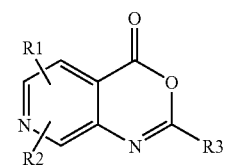

pyrido[2,3-d][1,3]oxazin-4-ones with the formula

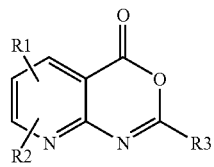

pyrazino[2,3-d][1,3]oxazin-4-ones with the formula

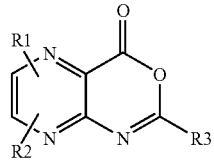

pyrimido[4,5-d][1,3]oxazin-4-ones with the formula

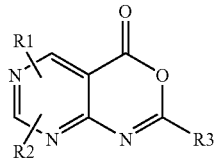

pyrrolo[3,4-d][1,3]oxazin-4-ones with the formula

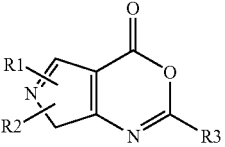

pyrazolo[3,4-d][1,3]oxazin-4-ones with the formula

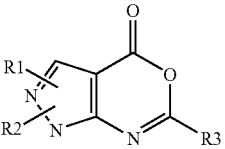

imidazo[4,5-d][1,3]oxazin-4-ones with the formula

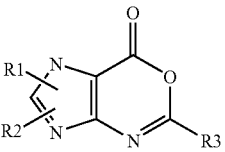

pyrazolo[4,3-d][1,3]oxazin-4-ones with the formula

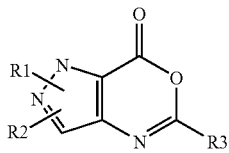

furo[2,3-d][1,3]oxazin-4-ones with the formula

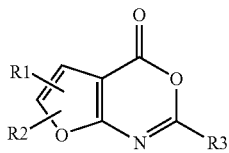

furo[3,4-d][1,3]oxazin-4-ones with the formula

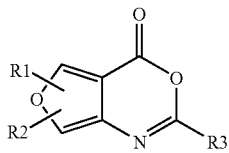

furo[3,2-d][1,3]oxazin-4-ones with the formula

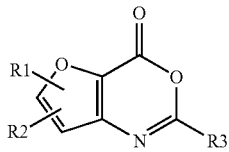

Among the above-mentioned examples of preferred compounds of formula Ia or IIa, the following compounds are particularly preferred ($R_1$, $R_2$, $R_3$ as defined above):

benzo[d][1,3]oxazin-4-ones with the formula

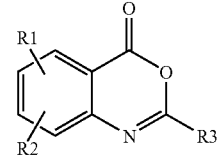

benzo[e][1,3]oxazin-4-ones with the formula

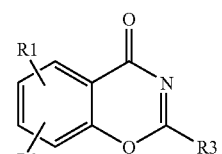

thieno[3,2-d][1,3]oxazin-4-ones with the formula

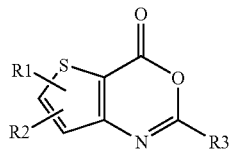

thieno[2,3-d][1,3]oxazin-4-ones with the formula

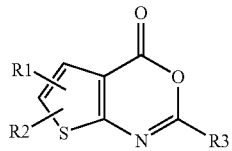

thieno[2,3-e][1,3]oxazin-4-ones with the formula

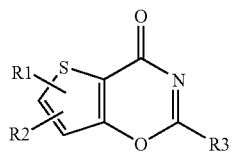

thieno[3,2-e][1,3]oxazin-4-ones with the formula

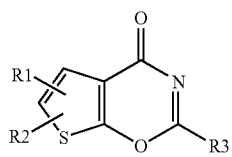

Isothiazolo[5,4-d][1,3]oxazin-4-ones with the formula

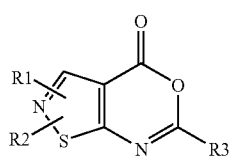

pyrazolo[3,4-d][1,3]oxazin-4-ones with the formula

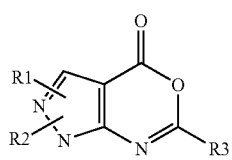

The $R_1$ and $R_2$ Substituents

As indicated above $R_1$ and $R_2$, if present, are independently $C_{1-8}$-alkyl, $C_{2-8}$-alkenyl, $C_{2-8}$-alkynyl or $C_{3-6}$-cycloalkyl, each optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; H, halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, or tetrazole;

or $R_1$ and $R_2$, when bonded to adjacent atoms in ring A or ring C, together form a moiety —$(CH_2)_n$—, where n=1-5, and wherein 1, 2 or 3 $CH_2$ units in said moiety are optionally replaced by 1, 2 or 3 heteroatoms, wherein each heteroatom is individually selected from the group consisting of O, S, NH and N if the nitrogen atom is bonded to an adjacent atom via a double bond, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$ alkoxy, trifluoromethoxy, carbamoyl, $CONHR_4$, or $CON(R_4)_2$.

In a preferred embodiment of the invention $R_1$ and $R_2$, if present, independently are $C_{1-8}$-alkyl optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; halogen, $C_{1-6}$-alkoxy;

or $R_1$ and $R_2$, when bonded, to adjacent atoms, together form a moiety —$(CH_2)_n$—, where n=3, 4 or 5, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$-alkoxy, trifluoromethoxy, carbamoyl, $CONHR_4$, or $CON(R_4)_2$.

As far compounds of the general formula I or Ia are concerned, $R_1$ and $R_2$, if present, are most preferably $C_{1-8}$-alkyl optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; halogen or $C_{1-6}$-alkoxy, in particular F, Cl, Br, I, O—$CH_3$ or O—$CH_2$—$CH_3$, such as Cl or O—$CH_3$. In one embodiment of the invention none of $R_1$ and $R_2$ are present. In another embodiment only one of $R_1$ and $R_2$ is present. In still another embodiment both of $R_1$ and $R_2$ are present. In general, it is preferred that that at least one of $R_1$ and $R_2$ is present.

As far compounds of the general formula II or IIa are concerned, $R_1$ and $R_2$, if present, are most preferably $C_{1-8}$-alkyl optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$;

or $R_1$ and $R_2$, when bonded to adjacent atoms, together form a moiety —$(CH_2)_n$—, where n=3, 4 or 5, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$-alkoxy, trifluoromethoxy, carbamoyl, $CONHR_4$, or $CON(R_4)_2$. Particular preferred examples include —$CH_3$, —$CH_2$—$CH_3$ as well as 5,6,7,8-tetrahydro-3-oxa-9-thia-1-aza-fluorene-4-ones with the formula

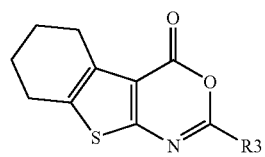

5,6,7,8-tetrahydro-1-oxa-9-thia-3-aza-fluorene-4-ones with the formula

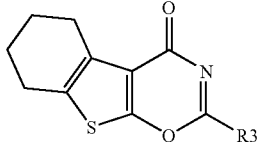

5,6,7,8-tetrahydro-3,9-dioxa-1-aza-fluorene-4-ones with the formula

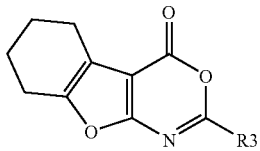

5,6,7,8-tetrahydro-5H-3-oxa-1,9-diaza-fluorene-4-ones with the formula

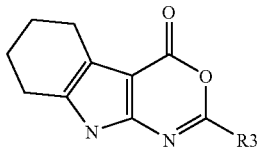

2,9-Dioxa-4-aza-fluoren-1-ones with the formula

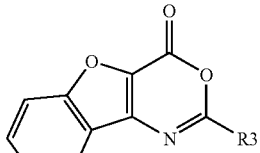

2,3-dihydro-1H-5-oxa-8-thia-7-aza-cyclopenta[a]indene-4-ones with the formula

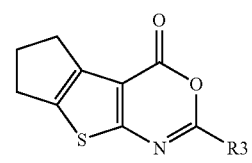

2,3-dihydro-1H-7-oxa-8-thia-5-aza-cyclopenta[a]indene-4-ones with the formula

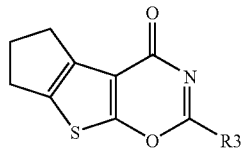

2,3-dihydro-1H-5,8-dioxa-7-aza-cyclopenta[a]indene-4-ones with the formula

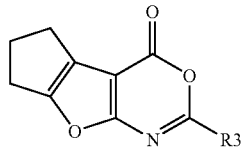

1,2,3,8-tetrahydro-5-oxa-7,8-diaza-cyclopenta[a]indene-4-ones with the formula

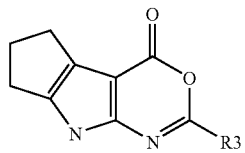

6,7,8,9-tetrahydro-5H-3-oxa-10-thia-1-aza-benzo[a]azulen-4-ones with the formula

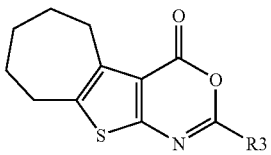

6,7,8,9-tetrahydro-5H-1-oxa-10-thia-3-aza-benzo[a]azulen-4-ones with the formula

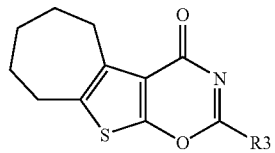

6,7,8,9-tetrahydro-5H-3,10-dioxa-1-aza-benzo[a]azulen-4-ones with the formula

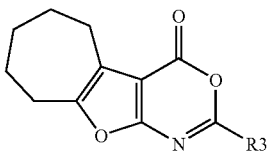

5,6,7,8,9,10-hexahydro-3-oxa-1,10-diaza-benzo[a]azulen-4-ones with the formula

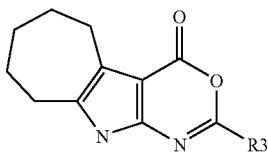

As far as formulas II and IIa are concerned, another interesting embodiment of the invention includes the example where none of $R_1$ and $R_2$ are present.

Preferred examples of $R_4$ include methyl, ethyl, isopropyl, propyl, cyclopropyl, cyclopentyl, cyclohexyl and phenyl.

The $R_3$ Substituent

As indicated above $R_3$ is aryl or heteroaryl, each optionally substituted with one or more halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, tetrazole, $C_{1-8}$-alkyl, $C_{2-8}$-alkenyl, $C_{2-8}$-alkynyl or $C_{3-6}$-cycloalkyl, each $C_{1-8}$-alkyl, $C_{2-8}$-alkenyl, $C_{2-8}$-alkynyl or $C_{3-6}$-cycloalkyl being optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl.

More preferably, $R_3$ is phenyl, 1-naphtyl, 4-pyridinyl, 2-furanyl or 2-thienyl, each optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl; halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$alkoxycarbonyl, aryl, aryloxy, heteroaryl, heteroaryloxy, alkylphenyl, or tetrazole; Specific examples of preferred substituted aryl or heteroaryl groups include phenyl, 2-fluorophenyl, 2-chlorophenyl, 2-iodophenyl, 2-methoxyphenyl, 3-methoxyphenyl, 2-hydroxyphenyl, 1-naphthyl, 2-tolyl, 2-chloro-4-nitrophenyl, 2-chloro-5-nitrophenyl, 4-fluorophenyl, 4-bromophenyl, 2-thienyl, 2-furanyl and 4-pyridinyl.

In general, it is preferred that the aryl or heteroaryl group is substituted with at least one electron-withdrawing group, such as fluorine, chlorine; $NO_2$, $CF_3$ and $OCF_3$. Most preferred is chlorine and fluorine, in particular chlorine. Furthermore, $R_3$ is preferably an ortho-substituted aryl (mono- or disubstituted) or a heteroaryl ring. Preferred ortho-substituents are: fluoro, chloro, iodo, bromo, methyl, methoxy, hydroxy, acetoxy, or $NHSO_2$-aryl.

EXAMPLES OF SPECIFIC AND PREFERRED COMPOUNDS

Specific examples of preferred compounds of formula I which are suitable for the purposes described herein include

| | |
|---|---|
| 2-Phenyl-benzo[d][1,3]oxazin-4-one | (I-1) |
| 7-Chloro-2-(2-chloro-4-nitro-phenyl)-benzo[d][1,3]oxazin-4-one | (I-2) |
| 2-(2-Iodo-phenyl)-6,7-dimethoxy-benzo[d][1,3]oxazin-4-one | (I-3) |
| 7-Chloro-2-thiophen-2-yl-benzo[d][1,3]oxazin-4-one | (I-4) |
| 2-(2-Chloro-4-nitro-phenyl)-6,7-dimethoxy-benzo[d][1,3]oxazin-4-one | (I-5) |
| 2-(2-Chloro-5-nitro-phenyl)-benzo[d][1,3]oxazin-4-one | (I-6) |
| 5,7-Dichloro-2-(dimethylamino-benz[d][1,3]oxazin-4-one | (I-7) |
| 2-Pyridin-4-yl-benzo[d][1,3]oxazin-4-one | (I-8) |
| 2-Thiophen-2-yl-benzo[d][1,3]oxazin-4-one | (I-9) |
| 2-(2-Hydroxy-phenyl)-benzo[d][1,3]oxazin-4-one | (I-10) |
| 2-(2-Fluoro-phenyl)-6,7-dimethoxy-benzo[d][1,3]oxazin-4-one | (I-11) |
| 7-Chloro-2-(4-ethyl-phenyl)benzo[d][1,3]oxazin-4-one | (I-12) |
| 7-Chloro-2-(3-methyl-4-nitro-phenyl)-benzo[d][1,3]oxazin-4-one | (I-13) |
| N-[4-(6,7-Dimethoxy-4-oxo-4H-benzo[d][1,3]oxazin-2-yl)-phenyl]-acetamide | (I-14) |
| Acetic acid 4-(4-oxo-4H-benzo[d][1,3]oxazin-2-yl)-phenyl ester | (I-15) |
| 2-(2-Chlorophenyl)-6,7-dimethoxy-benzo[d][1,3]oxazin-4-one | (I-16) |
| 6-Chloro-2-thiophen-2-yl-benzo[e][1,3]oxazin-4-one | (I-17) |
| 6-Chloro-2-furan-2-yl-benzo[e][1,3]oxazin-4-one | (I-18) |
| 2-(2-Chlorophenyl)-benzo[e][1,3]oxazin-4-one | (I-19) |
| 2-Thiophen-2-yl-benzo[e][1,3]oxazin-4-one | (I-20) |
| 2-Furan-2-yl-benzo[e][1,3]oxazin-4-one | (I-21) |

Examples of particular preferred compounds of formula I include

| | |
|---|---|
| 7-Chloro-2-(2-chloro-4-nitro-phenyl)-benzo[d][1,3]oxazin-4-one | (I-2) |
| 2-(2-Iodo-phenyl)-6,7-dimethoxy-benzo[d][1,3]oxazin-4-one | (I-3) |
| 7-Chloro-2-thiophen-2-yl-benzo[d][1,3]oxazin-4-one | (I-4) |
| 2-(2-Chloro-4-nitro-phenyl)-6,7-dimethoxy-benzo[d][1,3]oxazin-4-one | (I-5) |
| 2-(2-Chloro-5-nitro-phenyl)-benzo[d][1,3]oxazin-4-one | (I-6) |
| 2-(2-Fluoro-phenyl)-6,7-dimethoxy-benzo[d][1,3]oxazin-4-one | (I-11) |
| 2-(2-Chlorophenyl)-6,7-dimethoxy-benzo[d][1,3]oxazin-4-one | (I-16) |
| 6-Chloro-2-thiophen-2-yl-benzo[e][1,3]oxazin-4-one | (I-17) |
| 6-Chloro-2-furan-2-yl-benzo[e][1,3]oxazin-4-one | (I-18) |

Preferred Compounds with formula II are:

| | |
|---|---|
| 6-Ethyl-2-(2-fluoro-phenyl)-thieno[2,3-d][1,3]oxazin-4-one | (II-1) |

6-Methyl-2-naphthalen-1-yl-thieno[2,3-d][1,3]oxazin-4-one (II-2)

6-Ethyl-2-o-tolyl-thieno[2,3-d][1,3]oxazin-4-one (II-3)

6-Ethyl-2-(4-fluoro-phenyl)-thieno[2,3-d][1,3]oxazin-4-one (II-4)

2-(2-chloro-phenyl)-4H-thieno[3,2-d][1,3]Oxazin-4-one (II-5)

2-phenyl-4H-thieno[3,2-d][1,3]oxazin-4-one (II-6)

2-Furan-2-yl-5,6-dimethyl-thieno[2,3-d][1,3]oxazin-4-one (II-7)

2-(4-fluoro-phenyl)-4H-thieno[3,2-d][1,3]oxazin-4-one (II-8)

2-(4-Bromo-phenyl)-6-ethyl-thieno[2,3-d][1,3]oxazin-4-one (II-9)

6-(2-Chloro-phenyl)-2,3-dihydro-1H-5-oxa-8-thia-7-aza-cyclopenta[a]indene-4-one (II-10)

6-Furan-2-yl-2,3-dihydro-1H-5-oxa-8-thia-7-aza-cyclopenta[a]inden-4-one (II-11)

6-Phenyl-2,3-dihydro-1H-5-oxa-8-thia-7-aza-cyclopenta[a]inden-4-one (II-12)

6-(4-Fluoro-phenyl)-2,3-dihydro-1H-5-oxa-8-thia-7-aza-cyclopenta[a]inden-4-one (II-13)

6-Thiophen-2-yl-2,3-dihydro-1H-5-oxo-8-thia-7-aza-cyclopenta[a]inden-4-one (II-14)

2-(2-Fluoro-phenyl)-5,6,7,8-tetrahydro-3-oxa-9-thia-1-aza-fluoren-4-one (II-15)

2-(2-Methoxy-phenyl)-5,6,7,8-tetrahydro-3-oxa-9-thia-1-aza-fluoren-4-one (II-16)

2-Phenyl-5,6,7,8-tetrahydro-3-oxa-9-thia-1-aza-fluoren-4-one (II-17)

2-Naphthalen-1-yl-5,6,7,8-tetrahydro-3-oxa-9-thia-1-aza-fluoren-4-one (II-18)

2-Thiophen-2-yl-5,6,7,8-tetrahydro-3-oxa-9-thia-1-aza-fluoren-4-one (II-19)

2-(3-Methoxy-phenyl)-5,6,7,8-tetrahydro-3-oxa-9-thia-1-aza-fluoren-4-one (II-20)

2-Pyridin-4-yl-6,7,8,9-tetrahydro-5H-3-oxa-10-thia-1-aza-benzo[a]azulen-4-one (II-21)

Examples of particular preferred compounds of formula II include:

6-Ethyl-2-(2-fluoro-phenyl)-thieno[2,3-d][1,3]oxazin-4-one (II-1)

6-Methyl-2-naphthalen-1-yl-thieno[2,3-d][1,3]oxazin-4-one (II-2)

6-Ethyl-2-o-tolyl-thieno[2,3-d][1,3]oxazin-4-one (II-3)

6-Ethyl-2-(4-fluoro-phenyl)-thieno[2,3-d][1,3]oxazin-4-one (II-4)

2-(2-chloro-phenyl)-4H-thieno[3,2-d][1,3]oxazin-4-one (II-5)

6-(2-Chloro-phenyl)-2,3-dihydro-1H-5-oxa-8-thia-7-aza-cyclopenta[a]indene-4-one (II-10)

6-Furan-2-yl-2,3-dihydro-1H-5-oxa-8-thia-7-aza-cyclopenta[a]inden-4-one (II-11)

6-Phenyl-2,3-dihydro-1H-5-oxa-8-thia-7-aza-cyclopenta[a]inden-4-one (II-12)

6-(4-Fluoro-phenyl)-2,3-dihydro-1H-5-oxa-8-thia-7-aza-cyclopenta[a]inden-4-one (II-13)

6-Thiophen-2-yl-2,3-dihydro-1H-5-oxo-8-thia-7-aza-cyclopenta[a]inden-4-one (II-14)

2-(2-Fluoro-phenyl)-5,6,7,8-tetrahydro-3-oxa-9-thia-1-aza-fluoren-4-one (II-15)

2-(2-Methoxy-phenyl)-5,6,7,8-tetrahydro-3-oxa-9-thia-1-aza-fluoren-4-one (II-16)

2-Phenyl-5,6,7,8-tetrahydro-3-oxa-9-thia-1-aza-fluoren-4-one (II-17)

Manufacture

The compounds with general formula I and II may be prepared from compounds having formulas III or IV or V/VI or VII or VIII by the following methods:

Method A):

1) Reacting a compound of formula III

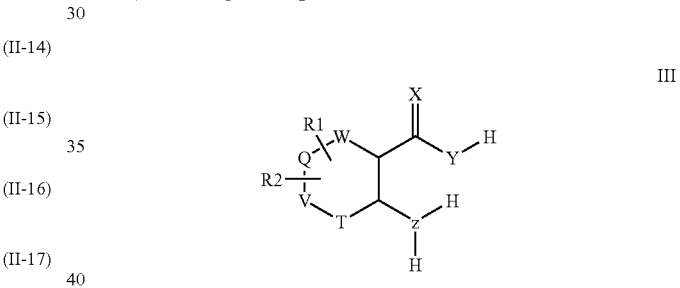

III with a compound of the formula $R_3COL$; $R_1$, $R_2$, $R_3$, Z, X, Y, W, Q, V and T having the meanings as defined above, L being a leaving group such as halogen, sulphate or acyl group, under formation of a structure IV;

2) reacting a compound of formula IV

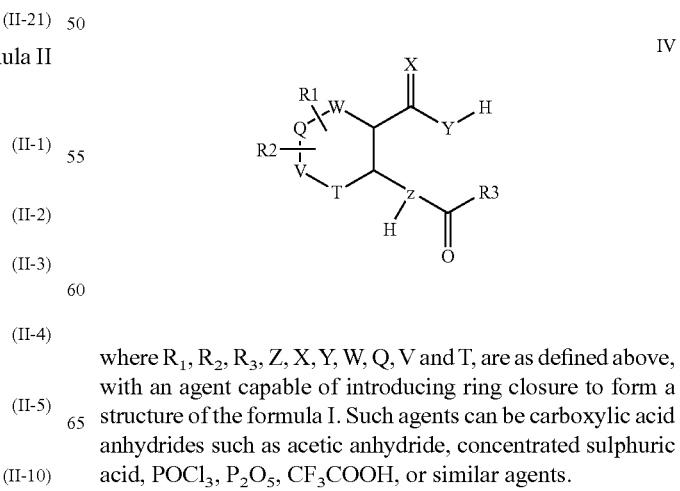

IV where $R_1$, $R_2$, $R_3$, Z, X, Y, W, Q, V and T, are as defined above, with an agent capable of introducing ring closure to form a structure of the formula I. Such agents can be carboxylic acid anhydrides such as acetic anhydride, concentrated sulphuric acid, $POCl_3$, $P_2O_5$, $CF_3COOH$, or similar agents.

Method B):

1) Reacting a compound of formula III

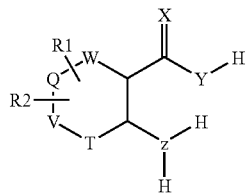

III with a compound of the formula $R_3COOH$; $R_1$, $R_2$, $R_3$, Z, X, Y, W, Q, V and T having the meanings as defined above; using a standard coupling agent such as HOBt or a carbodiimide such as DCC or EDAC, or similar agents suitable for formation of amide bonds from acids or activated acids and amines, under formation of a structure IV;

2) reacting a compound of formula IV

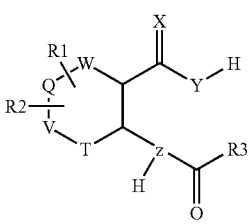

IV where are $R_1$, $R_2$, $R_3$, Z, X, Y, W, Q, V and T as defined above, with an agent capable of introducing ring closure to form a structure of the formula I. Such agents can be carboxylic acid anhydrides such as acetic anhydride, concentrated sulphuric acid, $POCl_3$, $P_2O_5$, $CF_3COOH$, or similar agents.

Method C):

Reacting a compound of formula IV

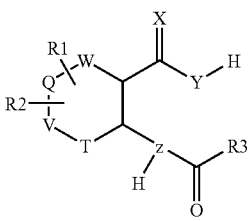

IV where $R_1$, $R_2$, $R_3$, Z, X, Y, W, Q, V and T are as defined above, with an agent capable of introducing ring closure to form a structure of the formula I. Such agents can be carboxylic acid anhydrides such as acetic anhydride, concentrated sulphuric acid, $POCl_3$, $P_2O_5$, $CF_3COOH$, or similar agents.

Method D):

Reacting a compound of formula V

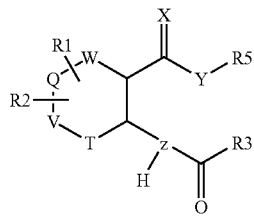

V where $R_1$, $R_2$, $R_3$, Z, X, Y, W, Q, V and T are as defined above and $R_5$ is an $C_{1-8}$ alkyl group, with an agent capable of introducing ring closure such as concentrated $H_2SO_4$ or $PPh_3/Et_3N/C_2Cl_4Br_2$, or similar agents which can introduce combined hydrolysis and ring closure under absorption of water, under formation of a compound of structure I.

Method E):

1) Reacting a compound of formula VI

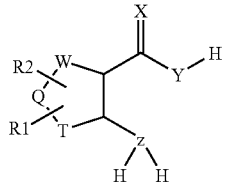

VI with a compound of the formula $R_3COL$; $R_1$, $R_2$, $R_3$, Z, X, Y, W, Q and T having the meanings as defined above, L being a leaving group such as halogen, sulphate or acyl group, under formation of a structure VII;

2) reacting a compound of formula VII

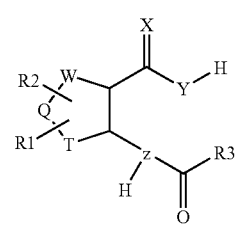

VII where $R_1$, $R_2$, $R_3$, Z, X, Y, W, Q and T are as defined above, with an agent capable of introducing ring closure to form a structure of the formula II. Such agents can be carboxylic acid anhydrides such as acetic anhydride, concentrated sulphuric acid, $POCl_3$, $P_2O_5$, $CF_3COOH$, or similar agents.

Method F):

1) Reacting a compound of formula VI

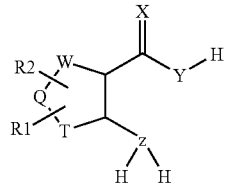

VI with a compound of the formula $R_3COOH$; $R_1$, $R_2$, $R_3$, Z, X, Y, W, Q and T having the meanings as defined above; using a standard coupling agent such as HOBt or a carbodiimide such as DCC or EDAC, or similar agents suitable for formation of amide bonds from acids or activated acids and amines, under formation of a structure VII;

2) reacting a compound of formula VII

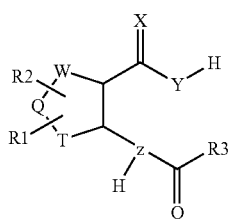

VII where $R_1$, $R_2$, $R_3$, Z, X, Y, W, Q and T are as defined above, with an agent capable of introducing ring closure to form a structure of the formula II. Such agents can be carboxylic acid anhydrides such as acetic anhydride, concentrated sulphuric acid, $POCl_3$, $P_2O_5$, $CF_3COOH$, or similar agents.

Method G):

Reacting a compound of formula VII

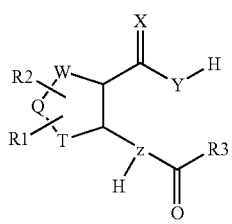

VII where $R_1$, $R_2$, $R_3$, Z, X, Y, W, Q and T are as defined above, with an agent capable of introducing ring closure to form a structure of the formula II. Such agents can be carboxylic acid anhydrides such as acetic anhydride, concentrated sulphuric acid, $POCl_3$, $P_2O_5$, $CF_3COOH$, or similar agents.

Method H):

Reacting a compound of formula VIII

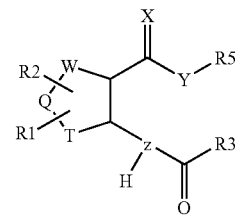

VIII where $R_1$, $R_2$, $R_3$, Z, X, Y, W, Q and T are as defined above and $R_5$ is an $C_{1-28}$ alkyl group, with an agent capable of introducing ring closure such as concentrated $H_2SO_4$ or $PPh_3/Et_3N/C_2Cl_4Br_2$, or similar agents which can introduce combined hydrolysis and ring closure under absorption of water, under formation of a compound of structure II.

Examples of the synthetic methods described above are known to the person skilled in the art and described several times in the literature; see for example E. P. Papadopoulos and C. D. Torres: *Heterocycles* 19 (6) 1039-1042, 1982;

J. L. Gilmore et al: *Bioorganic and Medicinal Chemistry Letters* 6 (6), 679-682, 1996;

M Davies, R. J. Hook, Wen Yang Wu: *J Heterocyclic Chem* 21 369-373, 1984;

G. Hamprecht, B. Wuerzer: U.S. Pat. No. 4,315,766, 1982;

H. Wamhoff; E. Kroth: *Synthesis* 405, 1994.

The synthesis of the following example of compounds of the general formula I are described in WO 99/48878. These compounds are examples of compounds of the general formula I which can be used according to the present invention.

5,8-Dichloro-2-(2-fluoro-phenyl)-4H-3,1-benzoxazin-4-one,
6-Methyl-2-thiophen-2-yl-4H-3,1-benzoxazin-4-one,
(2,6-Dichloro-phenyl)-6-methyl-4H-3,1-benzoxazin-4-one,
6-Methyl-2-(2-trifluoromethoxy-phenyl)-4H-3,1-benzoxazin-4-one,
(2,6-Difluoro-phenyl)-6-methyl-4H-3,1-benzoxazin-4-one,
(2,6-Dimethoxy-phenyl)-6-methyl-4H-3,1-]benzoxazin-4-one,
(3-Bromo-thiophen-2-yl)-6-methyl-4H-3,1-benzoxazin-4-one,
(2,3-Dichloro-phenyl)-6-methyl-4H-3,1-benzoxazin-4-one,
2-(2,6-Difluoro-phenyl)-6-nitro-benzo[d][1,3]oxazin-4-one,
6-Acetamido-(2,6-difluoro-phenyl)-benzo[d][1,3]oxazin-4-one,
2-(2,6-Difluoro-phenyl)-5-methyl-benzo[d][1,3]oxazin-4-one,
2-(2,6-Difluoro-phenyl)-7-nitro-benzo[d][1,3]oxazin-4-one,
2-(2,6-Difluoro-phenyl)-5-nitro-benzo[d][1,3]oxazin-4-one,
5-Chloro-2-(2,6-difluoro-phenyl)-benzo[d][1,3]oxazin-4-one,
6-Amino-2-(2,6-difluoro-phenyl)-benzo[d][1,3]oxazin-4-one,
2-(2,6-Difluoro-phenyl)-8-hydroxy-benzo[d][1,3]oxazin-4-one,
5,8-Dichloro-2-(2,6-difluoro-phenyl)-benzo[d][1,3]oxazin-4-one,
5-Amino-2-(2,6-difluoro-phenyl)-benzo[d][1,3]oxazin-4-one,
2-(2,6-Difluoro-phenyl)-6,7-difluoro-benzo[d][1,3]oxazin-4-one, 7-Amino-2-(2,6-difluoro-phenyl)-benzo[d][1,3]oxazin-4-one,
2-(2,6-Difluoro-phenyl)-6-methoxy-benzo[d][1,3]oxazin-4-one,
2-(2-Fluoro-phenyl)-6-methoxy-benzo[d][1,3]oxazin-4-one,
2-(2,6-Difluoro-phenyl)-7-trifluoromethyl-benzo[d][1,3]oxazin-4-one,
6,7-Difluoro-2-(2-fluoro-phenyl)-benzo[d][1,3]oxazin-4-one,
6,7-Difluoro-2-thiophen-2-yl-benzo[d][1,3]oxazin-4-one,
6,7-Difluoro-2-furan-2-yl-benzo[d][1,3]oxazin-4-one,
2-(2-Methoxy-phenyl)-6-nitro-benzo[d][1,3]oxazin-4-one,
2-(2-Methoxy-phenyl)-5-methyl-benzo[d][1,3]oxazin-4-one,
2-(2-Methoxy-phenyl)-5-nitro-benzo[d][1,3]oxazin-4-one,
6-Nitro-2-(2-nitro-phenyl)-benzo[d][1,3]oxazin-4-one,
6-Nitro-2-o-tolyl-benzo[d][1,3]oxazin-4-one,
5-Nitro-2-(2-nitro-phenyl)-benzo[d][1,3]oxazin-4-one,
5-Nitro-2-(2-nitro-phenyl)-benzo[d][1,3]oxazin-4-one,
2-(2-Chloro-pyridin-3-yl)-6-nitro-benzo[d][1,3]oxazin-4-one,
2-(2-Chloro-pyridin-3-yl)-5-methyl-benzo[d][1,3]oxazin-4-one,
2-(2-Chloro-pyridin-3-yl)-5-nitro-benzo[d][1,3]oxazin-4-one,
2-(2,3-Difluoro-phenyl)-6-nitro-benzo[d][1,3]oxazin-4-one,
2-(2,3-Difluoro-phenyl)-5-methyl-benzo[d][1,3]oxazin-4-one,
2-(2,3-Difluoro-phenyl)-5-nitro-benzo[d][1,3]oxazin-4-one,
2-(2,6-Difluoro-phenyl)-6-trifluoromethyl-benzo[d][1,3]oxazin-4-one,
2-(2-Fluoro-phenyl)-6-trifluoromethyl-benzo[d][1,3]oxazin-4-one,
2-Thiophen-2-yl-6-trifluoromethyl-benzo[d][1,3]oxazin-4-one,
2-(2,6-Difluoro-phenyl)-5-trifluoromethyl-benzo[d][1,3]oxazin-4-one,
2-(2-Fluoro-phenyl)-5-trifluoromethyl-benzo[d][1,3]oxazin-4-one,
2-Thiophen-2-yl-5-trifluoromethyl-benzo[d][1,3]oxazin-4-one,
2-(2,6-Difluoro-phenyl)-8-trifluoromethyl-benzo[d][1,3]oxazin-4-one,
2-(2-Fluoro-phenyl)-8-trifluoromethyl-benzo[d][1,3]oxazin-4-one,
2-Furan-2-yl-8-trifluoromethyl-benzo[d][1,3]oxazin-4-one,
2-(2,6-Difluoro-phenyl)-7-fluoro-benzo[d][1,3]oxazin-4-one,
5-Nitro-2-(5-nitro-furan-2-yl)-benzo[d][1,3]oxazin-4-one,
2-(2,3-Dichloro-phenyl)-6,7-difluoro-benzo[d][1,3]oxazin-4-one,
6,7-Difluoro-2-(2-trifluoromethoxy-phenyl)-benzo[d][1,3]oxazin-4-one,
2-(2,3-Difluoro-phenyl)-6,7-difluoro-benzo[d][1,3]oxazin-4-one,
6,7-Difluoro-2-(2-methoxy-phenyl)-benzo[d][1,3]oxazin-4-one,
2-(2-Chloro-pyridin-3-yl)-6,7-difluoro-benzo[d][1,3]oxazin-4-one,
2-(2,6-Difluoro-phenyl)-4-oxo-4H-benzo[d][1,3]oxazine-5-carboxylic acid methyl ester,
2-(2-Fluoro-phenyl)-4-oxo-4H-benzo[d][1,3]oxazine-5-carboxylic acid methyl ester,
4-Oxo-2-thiophen-2-yl-4H-benzo[d][1,3]oxazine-5-carboxylic acid methyl ester,
2-Furan-2-yl-4-oxo-4H-benzo[d][1,3]oxazine-5-carboxylic acid methyl ester,
2-(2-Fluoro-phenyl)-4-oxo-4H-benzo[d][1,3]oxazine-5-carboxylic acid ethyl ester,
Acetic acid 2-(6-nitro-4-oxo-4H-benzo[d][1,3]oxazin-2-yl)-phenyl ester,
Acetic acid 2-(5-methyl-4-oxo-4H-benzo[d][1,3]oxazin-2-yl)-phenyl ester,
Acetic acid 2-(5-nitro-4-oxo-4H-benzo[d][1,3]oxazin-2-yl)-phenyl ester.

The synthesis of the following example of compounds of the general formula I are described in WO 00/30646. These compounds are examples of compounds of the general formula I which can be used according to the present invention.

2-(2-Fluorophenyl)-4H-Pyrido[2,3-d][1,3]oxazin-4-one,
2-(2,6-Difluorophenyl)-4H-Pyrido[2,3-d][1,3]oxazin-4-one,
7-(Ethylthio)-2-(2-fluorophenyl)-4H-Pyrimido[4,5-d][1,3]oxazin-4-one,
7-(Ethylthio)-2-(2-methylphenyl)-4H-Pyrimido[4,5-d][1,3]oxazin-4-one,
2-(2-Chlorophenyl)-7-(ethylthio)-4H-Pyrimido[4,5-d][1,3]oxazin-4-one.

The synthesis of the following example of compounds of the general formula II are described in WO 00/30646. These compounds are examples of compounds of the general formula II which can be used according to the present invention.

2-(2,6-Difluoro-phenyl)-7-methyl-thieno[3,2-d][1,3]oxazin-4-one,
5-Methyl-2-(2-nitro-phenyl)-thieno[2,3-d][1,3]oxazin-4-one,
2-Furan-2-yl-thieno[2,3-d][1,3]oxazin-4-one,
2-Thiophen-2-yl-thieno[2,3-d][1,3]oxazin-4-one,
1-Methyl-6-(2-nitrophenyl)-Pyrazolo[3,4-d][1,3]oxazin-4(1H)-one,
6-(2-Fluorophenyl)-1-methyl-Pyrazolo[3,4-d][1,3]oxazin-4(1H)-one,
1-Methyl-6-(2-methylphenyl)-Pyrazolo[3,4-d][1,3]oxazin-4(1H)-one.

Some of the structures described in the present invention are commercially available from companies selling special chemicals. Examples are companies like Key Organics, Chemical Diversity, Sigma-Aldrich, Maybridge, Specs, CSC and Merlin Chemicals.

Examples of compounds of formula I are the following.
2-(2,5-Dimethyl-benzofuran-7-yl)-4H-3,1-benzoxazin-4-one,
2-(3-Bromo-phenyl)-4H-3,1-benzoxazin-4-one,
2-(3-Bromo-phenyl)-7-chloro-4H-3,1-benzoxazin-4-one,
2-(2,4-Dichloro-phenyl)-4H-3,1-benzoxazin-4-one,
2-(2-Fluoro-phenyl)-6-methyl-3,1-benzoxazin-4-one,
Naphthalene-2-sulfinic acid [2-(4-oxo-4H-3,1-benzoxazin-2-yl)-phenyl]-amide,
2-(4-Chloro-3-nitro-phenyl)-6,7-dimethoxy-4H-3,1-benzoxazin-4-one,
2-(5-Chloro-2-methoxy-phenyl)-4H-3,1-benzoxazin-4-one,
6-Bromo (5-chloro-2-methoxy-phenyl)-4H-3,1-benzoxazin-4-one,
2-(3,4-Dichloro-phenyl)-6,7-dimethoxy-4H-3,1-benzoxazin-4-one,
2-(3,4-Dimethyl-phenyl)-4H-3,1-benzoxazin-4-one,
7-Chloro-2-(4-methyl-3-nitro-phenyl)-4H-3,1-benzoxazin-4-one,
6,7-Dimethoxy-2-p-tolyl-4H-3,1-benzoxazin-4-one,
2-phenyl-4H-3,1-benzoxazin-4-one,
6,7,8-Trimethoxy-2-(3-trifluoromethyl-phenyl)-4H-3,1-benzoxazin-4-one, 6,7-Dimethoxy-2-[2-(4-methoxy-phenoxy)-5-nitro-phenyl]-4H-3,1-benzoxazin-4-one,
5-Chloro-2-[2-(4-methoxy-phenoxy)-5-nitro-phenyl]-4H-3,1-benzoxazin-4-one,
2-(4-tert-Butyl-phenyl)-7-chloro-4H-3,1-benzoxazin-4-one,
7-Chloro-2-m-tolyl-4H-3,1-benzoxazin-4-one,
6,7-Dimethoxy-2-(5-methyl-2-nitro-phenyl)-4H-3,1-benzoxazin-4-one,
7-Chloro-2-(4-chloro-3-nitro-phenyl)-4H-3,1-benzoxazin-4-one,
2-(3,4-Dimethyl-phenyl)-6,7-dimethoxy-4H-3,1-benzoxazin-4-one,
7-Chloro-2-[4-(5-ethyl-pyridin-2-yl)-phenyl]-4H-3,1-benzoxazin-4-one,
2-(4-Chloro-3-nitrophenyl)-6,7,8-trimethoxy-4H-3,1-benzoxazin-4-one,
2-(2,6-Difluorophenyl)-5-fluoro-4H-3,1-benzoxazin-4-one,
2-(2-Fluorophenyl)-4H-3,1-benzoxazin-4-one,
5-Chloro-2-(3-trifluoromethylphenyl)-4H-3,1-benzoxazin-4-one,
2-(3,4-Dichloro-phenyl)-6-nitro-4H-3,1-benzoxazin-4-one,
2-(2-Chloro-6-fluorophenyl)-5-fluoro-3,1-benzoxazin-4-one,
7-Chloro-2-(2-fluorophenyl)-3,1-benzoxazin-4-one,
2-(2-Chloro-6-fluorophenyl)-6-methyl-4H-3,1-benzoxazin-4-one,
2(2-(4-Fluorophenylsulfonyl)amidophenyl)-4H-3,1-benzoxazin-4-one,
2-(2-Bromo-5-methoxy-phenyl)-4H-3,1-benzoxazin-4-one,
2-(2-Chloromethyl-phenyl)-4H-3,1-benzoxazin-4-one,
2-(4-tert-Butyl-phenyl)-6,8-dimethyl-4H-3,1-benzoxazin-4-one,
2-(2-Chloro-phenyl)-6-methyl-4H-3,1-benzoxazin-4-one,
7-Chloro-2-(3-chloromethyl-phenyl)-4H-3,1-benzoxazin-4-one,
2-(2-Chloro-phenyl)-6-iodo-4H-3,1-benzoxazin-4-one,
7-Chloro-2-(2-chloro-5-nitro-phenyl)-4H-3,1-benzoxazin-4-one,
2-(2-Bromo-phenyl)-6-chloro-4H-3,1-benzoxazin-4-one,
6,7-Dimethoxy-2-(3-nitro-phenyl)-4H-3,1-benzoxazin-4-one,
2-(3-Nitro-phenyl)-4H-3,1-benzoxazin-4-one,
7-chloro-2-(2,4-dichlorophenyl)-4H-3,1-benzoxazin-4-one,
2-(2,4-Dichloro-phenyl)-6-iodo-4H-3,1-benzoxazin-4-one,
6-Bromo-2-(3-chloro-5-trifluoromethyl-pyridin-2-yl)-4H-3,1-benzoxazin-4-one,
6-(6,7-Dimethoxy-4-oxo-4H-3,1-benzoxazin-2-yl)-pyridine-2-carboxylic acid methyl ester,
6,7-Dimethoxy-2-pyridin-4-yl-4H-3,1-benzoxazin-4-one,
6-Bromo-2-pyridin-4-yl-4H-3,1-benzoxazin-4-one,
5-Fluoro-2-(2-phenoxy-pyridin-3-yl)-4H-3,1-benzoxazin-4-one,
6,7,8-Trimethoxy-2-(2-phenoxy-pyridin-3-yl)-4H-3,1-benzoxazin-4-one,
2-(3-Chloro-5-trifluoromethyl-pyridin-2-yl)-6,7-dimethoxy-4H-3,1-benzoxazin-4-one,
2-Thiophen-2-yl-4H-3,1-benzoxazin-4-one,
6,7,8-Trimethoxy-2-(5-nitro-furan-2-yl)-4H-3,1-benzoxazin-4-one,
6-Methyl-2-(5-nitro-furan-2-yl)-4H-3,1-benzoxazin-4-one,
5,8-Dichloro-2-(2-fluoro-phenyl)-4H-3,1-benzoxazin-4-one,
6-Methyl-2-thiophen-2-yl-4H-3,1-benzoxazin-4-one,
2-(2,6-Dichloro-phenyl)-6-methyl-4H-3,1-benzoxazin-4-one,
6-Methyl-2-(2-trifluoromethoxy-phenyl)-4H-3,1-benzoxazin-4-one,
2-(2,6-Difluoro-phenyl)-6-methyl-4H-3,1-benzoxazin-4-one,
2-(2,6-Dimethoxy-phenyl)-6-methyl-4H-3,1-benzoxazin-4-one,
2-(3-Bromo-thiophen-2-yl)-6-methyl-4H-3,1-benzoxazin-4-one,
2-(2,3-Dichloro-phenyl)-6-methyl-4H-3,1-benzoxazin-4-one,
2-(2,4-Dichloro-phenyl)-6-nitro-benzo[d][1,3]oxazin-4-one,
6,8-Dibromo-2-(2-fluoro-phenyl)-benzo[d][1,3]oxazin-4-one,
7-Chloro-2-(2-chloromethyl-phenyl)-4H-3,1-benzoxazin-4-one,
2-(4-chloro-phenyl)-6,7-dimethoxy-4H-3,1-benzoxazin-4-one,
2-(3-tolyl)-4H-3,1-benzoxazin-4-one,
2-(4-fluoro-phenyl)-4H-3,1-benzoxazin-4-one,
2-(4-chloro-phenyl)-4H-3,1-benzoxazin-4-one,
6,7 dibromo-2-phenyl-4H-3,1-benzoxazin-4-one,
2-(2-iodo-phenyl)-4H-3,1-benzoxazin-4-one,
2-(3,4,5-trimethoxy-phenyl)-4H-3,1-benzoxazin-4-one,
7-chloro-2-(3-methoxy-phenyl)-4H-3,1-benzoxazin-4-one,
7-chloro-2-(4-nitro-phenyl)-4H-3,1-benzoxazin-4-one,
2-(4-(tert-butyl)-phenyl)-4H-3,1-benzoxazin-4-one,
2-(3-chloro-phenyl)-4H-3,1-benzoxazin-4-one,
2-(2-chloro-4-nitro-phenyl)-4H-3,1-benzoxazin-4-one,
2-(4-chloro-2-nitro-phenyl)-4H-3,1-benzoxazin-4-one,
2-(2-chloro-3,5-dinitro-phenyl)-4H-3,1-benzoxazin-4-one,
2-(3,5-dinitro-2-methyl-phenyl)-4H-3,1-benzoxazin-4-one,
2-(3,4-dichloro-phenyl)-6-methyl-4H-3,1-benzoxazin-4-one,
2-(2,4-dinitro-phenyl)-4H-3,1-benzoxazin-4-one,
2-(3-chloro-phenyl)-6-methyl-4H-3,1-benzoxazin-4-one,
6-methyl-2-(4-nitro-phenyl)-4H-3,1-benzoxazin-4-one,
6-methyl-2-phenyl-4H-3,1-benzoxazin-4-one,
2-(3-methyl-4-nitro-phenyl)-4H-3,1-benzoxazin-4-one,
2-(4-chloro-3-nitro-phenyl)-4H-3,1-benzoxazin-4-one,
6-methyl-2-(3-tolyl)-4H-3,1-benzoxazin-4-one,
2-(2-tolyl)-4H-3,1-benzoxazin-4-one,
2-(3,5-dinitro-phenyl)-4H-3,1-benzoxazin-4-one,
2-(4-tolyl)-4H-3,1-benzoxazin-4-one,
2-(4-chloro-phenyl)-6-methyl-4H-3,1-benzoxazin-4-one,
2-(4-nitro-phenyl)-4H-3,1-benzoxazin-4-one,
2-(4-ethoxy-phenyl)-4H-3,1-benzoxazin-4-one,
2-(4-methyl-3-nitro-phenyl)-4H-3,1-benzoxazin-4-one,
6,8-dichloro-2-thiophen-2-yl-benzo[d][1,3]oxazin-4-one.
Examples of compounds of formula II are the following:
2-tert-Butyl-5,6,7,8-tetrahydro-3-oxa-9-thia-1-aza-fluoren-4-one,
2-(4-Bromo-phenyl)-5,6,7,8-tetrahydro-3-oxa-9-thia-1-aza-fluoren-4-one,
2-(4-Methoxy-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Methyl-5-thiophen-2-yl-thieno[2,3-d][1,3]oxazin-4-one,
2-Furan-2-yl-5-thiophen-2-yl-thieno[2,3-d][1,3]oxazin-4-one,
2-(2-Bromo-phenyl)-5,6,7,8-tetrahydro-3-oxa-9-thia-1-aza-fluoren-4-one,
2-Methyl-5,6,7,8-tetrahydro-3-oxa-9-thia-1-aza-fluoren-4-one,
2-(4-Chloro-phenyl)-5,6-dimethyl-thieno[2,3-d][1,3]oxazin-4-one,
2-Phenyl-5,6,7,8-tetrahydro-3-oxa-9-thia-1-aza-fluoren-4-one, 2-(3-Trifluoromethyl-phenyl)-thieno[3,2-d][1,3]oxazin-4-one,
2,5-diphenyl-4H-thieno[2,3-d][1,3]oxazin-4-one,
8-Chloro-2-phenyl-4H-Benzofuro[3,2-d][1,3]oxazin-4-one,
2-[4-(Trifluoromethyl)phenyl]-4H-Benzofuro[3,2-d][1,3]oxazin-4-one,
6-(2-Methylphenyl)-1-phenyl-Pyrazolo[3,4-d][1,3]oxazin-4(1H)-one,
6-(2-Fluorophenyl)-1-phenyl-Pyrazolo[3,4-d][1,3]oxazin-4(1H)-one,
6-(2-Chlorophenyl)-1-phenyl-Pyrazolo[3,4-d][1,3]oxazin-4(1H)-one.

Salts and Hydrates of the Compounds

Within the present invention, the compounds of formulas I and II may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid, ascorbic acid, embonic acid, methanesulphonic acid, malonic acid, and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan. The compounds of formulas I and II may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Pharmaceutical Compositions and Uses

In another aspect, the present invention includes within its scope pharmaceutical compositions comprising, as an active ingredient, at least one of the compounds with general formulas I and II or a pharmaceutically acceptable salt thereof together with a pharmaceutically acceptable carrier or diluent.

The compounds with general formulas I and II may be formulated into pharmaceutical composition comprising the compounds and a pharmaceutically acceptable carrier or diluent.

Such carriers include water, physiological saline, ethanol, polyols, e.g., glycerol or propylene glycol, or vegetable oils. As used herein, "pharmaceutically acceptable carriers" also encompasses any and all solvents, dispersion media, coatings, antifungal agents, preservatives, isotonic agents and the like. Except insofar as any conventional medium is incompatible with the active ingredient and its intended use, its use in the compositions of the present invention is contemplated.

The compositions containing the compounds with general formulas I and II may be prepared by conventional techniques and appear in conventional forms, for example, capsules, tablets, solutions or suspensions. The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water. Similarly, the carrier or diluent may include any time delay material known to the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as topical, oral or parenteral, e.g., rectal, transdermal, subcutaneous, intranasal, intramuscular, topical, intravenous, intraurethral, ophthalmic solution or an ointment, the oral route being preferred.

If a solid carrier for oral administration is used, the preparation can be tableted, placed in a hard gelatin, capsule in powder or pellet form or it can be in the form of a troche or lozenge.

The amount of solid carrier may vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, which may be prepared by conventional tabletting techniques, contains:

| Core. | |
|---|---|
| Active compound (as free compound or salt thereof) | 100 mg |
| Colloidal silicon dioxide (Areosil) | 1.5 mg |
| Cellulose, microcryst. (Avicele) | 70 mg |
| Modified cellulose gum (Ac-Di-Sol) | 7.5 mg |
| Magnesium stearate | |
| Coating. | |
| HPMC | approx. 9 mg |
| *Mywacett 9-40 T | approx. 0.9 mg |

*Acylated monoglyceride used as plasticizer for film coating.

Pharmaceutical compositions of the invention suitable for topical administration may be creams, ointments, lotions, liniments, gels, solutions, suspensions, pastes, sticks, sprays, shampoos, soaps, hair conditioners or powders.

The topical administration may be an administration onto or close to the parts of the body presenting the pathological changes in question, e.g. onto an exterior part of the body such as a skin surface. The application may be a simple smearing on of the composition, or it may involve any device suited for enhancing the establishment of contact between the composition and the pathological lesions such as the use of occlusive dressings, e.g. occlusion plasters provided with the composition of the invention. The compositions may be impregnated or distributed onto pads, plasters, strips, gauze, sponge materials, cotton wool pieces, etc. Optionally, a form of injection of the composition into or near the lesions may be employed.

The topical compositions according to the present invention may comprise 1-80% of the active compound by weight, based on the total weight of the preparations, such as 0.001-25% w/w of the active compound, e.g., 0.1-10%, 0.5-5%, or 2-5%. More than one active compound may be incorporated in the composition; i.e. compositions comprising a compound with general formulas I and II in combination with other pharmaceutical and/or cosmetic compounds are also within the scope of the invention. The composition is conveniently applied 1-10 times a day, depending on the type, severity and localization of the lesions.

For topical application, the preparation may be formulated in accordance with conventional pharmaceutical practice with pharmaceutical excipients conventionally used for topical applications. The nature of the vehicle employed in the preparation of any particular composition will depend on the method intended for administration of that composition. Vehicles other than water that can be used in compositions can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoridnoleate, glyceryl monostearate, propane 2-diol, butane-1,3-diol, cetyl alcohol, isopropyl isostearate, stearic acid, isobutyl palmitate, isocetyl stearate, oleyl alcohol, isopropyl laurate, hexyl laurate, decyl oleate, octadecanol, isocetyl alcohol, cetyl palmitate, dimethylpolysiloxane, di-n-butyl sebacate, isopropyl myristate, isopropyl palmitate, isopropylstearate, butyl stearate, polyethylene glycol, triethyleneglycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

solvents, such as water, methylene chloride, isopropanol, castor oil, ethylene glycol monoethyl ether, diethylene glycol monobutyl ether, diethylene glycol monoethyl ether, dimethyl sulfoxide, tetrahydrofuran, vegetable and animal oils, glycerol, ethanol, propanol, propylene glycol, and other glycols or alcohols, fixed oils;

humectants or moistening agents, such as glycerine, sorbitol, sodium 2-pyrrolidone carboxylate, soluble collagen, dibutyl phthalate, gelatine;

powders, such as chalk, talc, kaolin, starch and derivatives thereof, gums, colloidal silicon dioxide, sodium polyacrylate, chemically modified magnesium aluminium silicate, hydrated aluminium silicate, carboxyvinyl polymer, sodium carboxymethyl cellulose, ethylene glycol monostearate;

gelling or swelling agents, such as pectin, gelatine and derivatives thereof, cellulose derivatives such as methyl cellulose, carboxymethyl cellulose or oxidised cellulose, cellulose gum, quar gum, acacia gum, karaya gum, tragacanth gum, bentonite, agar, alginates, carbomer, gelatine, bladderwrack, ceratonia, dextran and derivatives thereof, ghatti gum, hectorite, ispaghula husk, xanthan gum;

polymers, such as polylactic acid or polyglycolic acid polymers or copolymers thereof, paraffin, polyethylene, polyethylene oxide, polyethylene glycol, polypropylene glycol, polyvinylpyrrolidone;

surfactants, such as non-ionic surfactants, e.g. glycol and glycerol esters, macrogol ethers and esters, sugar ethers and esters, such as sorbitan esters, ionic surfactants, such as amine soaps, metallic soaps, sulphated fatty alcohols, alkyl ether sulphates, sulphated oils, and ampholytic surfactants and lecitins;

buffering agents, such as sodium, potassium, aluminium, magnesium or calcium salts (such as the chloride, carbonate, bicarbonate, citrate, gluconate, lactate, acetate, gluceptate or tartrate).

For topical application, the pH of the composition may in principle be within a very broad range such as 3-9. In a preferred embodiment of the invention, a pH of about 4 to 8 is preferred. Conventional buffering agents as described above may be used to obtain the desired pH.

The preparation of the invention may also contain other additives such as stabilizing agents, preservatives, solubilizers, colouring agents, chelating agents, gel forming agents, ointment bases, pH-regulators, anti-oxidants, perfumes and skin protective agents, etc. If the composition is in the form of a shampoo or soap, the composition may further comprise foaming agents, pearling agents and/or conditioners.

Typical preservatives include the parabens, formaldehyde, Kathon CG, Bronidox, Bronopol, p-chloro-m-cresol, chlorhexidine, benzalkonium chloride, etc.

Conventional ingredients may be used where the compositions of the invention are in the form of a shampoo or a soap, and typical soap and shampoo bases include such components as betaine, sodium lauryl sulphate, nonyl phenol, imidazole, sulphosuccinate, refattening agents, humectants and conditioners.

Furthermore, it may be advantageous to provide modified release preparations in which the active compound is incorporated into a polymer matrix, or nanoparticles, or liposome or micelles, or adsorbed on Ion exchange resins, or carried by a polymer.

Compositions may be formulated according to conventional pharmaceutical practice and may be:

Semisolid formulations: Gels, pastes, mixtures;

Liquid formulations: Solutions, suspensions, drenches, emulsions.

As indicated, a pharmaceutical composition of the invention may comprise a compound of the invention itself or a functional derivative thereof, or a combination of such compounds. Examples of suitable functional derivatives include pharmaceutically acceptable salts, particularly those suitable for use in a cutaneous environment. Examples include pharmaceutically acceptable salts of the amino function, for example salts with acids yielding anions which are pharmaceutically acceptable, particularly in a cutaneous environment. Examples include phosphates, sulphates, nitrate, iodide, bromide, chloride, borate as well as anions derived from carboxylic acids including acetate, benzoate, stearate, etc.

Other derivatives of the amino function include amides, imides, ureas, carbamates, etc.

Other suitable derivatives include derivatives of the carboxyl group of the compounds of the invention, including salts, esters and amides. Examples include salts with pharmaceutically acceptable cations, e.g. lithium, sodium, potassium, magnesium, calcium, zinc, aluminium, ferric, ferrous, ammonium and lower ($C_{1-6}$)-alkyl ammonium salts. Esters include lower alkyl esters.

The examples of compositions below illustrate examples of pharmaceutical cosmetic and skin-care formulations according to the present invention, but should not in any way be limiting the scope of the compositions of the invention.

The cosmetic or skin care compositions comprising a compound with formula I or II is preferably in a form suitable for topical administration, and the composition is preferably in the form of a cream, an ointment, a lotion, a liniment, a gel, a paste, a stick, a spray, a shampoo, a soap, a hair conditioner or a powder. Such compositions may be prepared as described hereinbefore.

The cosmetic or skin care composition or the invention is suitable for treatment of cosmetic skin conditions, such as acne, xeroderma or other hyperkeratotic conditions, e.g., callosities and keratosis pilaris.

Accordingly, in a further aspect the invention relates to the use of a compound with formula I or II for treatment or prophylaxis of cosmetic skin conditions, such as acne, xeroderma or other hyperkeratotic conditions, e.g., callosities and keratosis pilaris.

In addition, the composition or the invention is suitable for treatment of skin diseases, in particular inflammatory skin diseases, such as atopic dermatitis, contact dermatitis, eczema, psoriasis, acne, epidermal hyperkeratosis, acanthosis, epidermal inflammation, dermal inflammation or pruritus. In particular, the skin disease may be pruritus.

Thus, in a still further aspect the invention relates to the use of a compound with the formula I or II for the manufacture of a medicament for the treatment of skin diseases, in particular inflammatory skin diseases, such as atopic dermatitis, contact dermatitis, eczema, psoriasis, acne, epidermal hyperkeratosis, acanthosis, epidermal inflammation, dermal inflammation or pruritus.

It will be understood that in a preferred embodiment of the invention, said compound and/or composition is administered topically.

In addition, it is contemplated that the composition of the invention may also be used for treatment of microbial infections as well as wound healing.

Moreover, it is envisaged that a compound of formula I or II is suitable for the treatment of cancer, in particular ovarian cancer. In an interesting embodiment of the invention said cancer is a carcinoma, such as a carcinoma selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors, in particular ovarian carcinoma.

Accordingly, in an even further aspect the invention relates to the use of a compound with the formula I or II, or a pharmaceutically acceptable salt thereof, for the manufacture of a medicament for the treatment of cancer, in particular for the treatment of ovarian cancer.

The compounds of formula I or II are effective over a wide dosage range. For example, in the treatment of adult humans, dosages from about 0.05 to about 100 mg, preferably from about 0.1 to about 100 mg per day may be used. A most preferable dosage is about 0.1 mg to about 70 mg per day. In choosing a regimen for patients, it may frequently be necessary to begin with a dosage of from about 20 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula I or formula II admixed with a pharmaceutically acceptable carrier or diluent.

The compounds may be administered concurrently, simultaneously, or together with a pharmaceutically acceptable carrier or diluent, whether by oral, rectal, or parenteral (including subcutaneous) route. The compounds are often, and preferably, in the form of an alkali metal or earth alkali metal salt thereof.

Suitable dosage ranges varies as indicated above depending upon the exact mode of administration, form in which administered, the indication towards which the administration is directed, the subject involved and the body weight of the subject involved, and the preference and experience of the physician or veterinarian in charge.

Apart from the therapeutic use of the compounds of formulas I and II, they may be useful in vitro tools for investigating the inhibition of SCCE activity.

The present invention is further illustrated by the following non-limiting examples.

EXAMPLES

Example 1

Methods for Identifying Inhibitory Compounds

Preparation of Active SCCE

Recombinant active human SCCE was produced essentially as described in WO 95/00651. The cDNA encoding human SCCE was introduced into a BPV vector under the control of the murine MT promoter and expressed in transfected C127 cells. The produced SCCE was purified and activated using immobilized bovine trypsin.

Identification of SCCE Inhibitors (the "SCCE Inhibitor Test")

SCCE activity was determined using the chromogenic substrate S-2586 (MeO-Suc-Arg-Pro-Tyr-pNA) (Chromogenix, Mölndal, Sweden) by measurement of the change in absorbance at 405 nm essentially as described in WO 95/00651. Inhibitors were dissolved in DMSO and added to the reaction mixture (10 mM sodium phosphate, pH 7.2, 0.5 M NaCl, 2.5 µg/ml SCCE) at appropriate concentrations followed by incubation for 10 min before the start of the enzymatic reaction by subsequent addition of the substrate S-2586 to a final concentration of 1 mM. The change in absorbance at 405 nm after 60 min was recorded and used as a measure of SCCE activity. The assay temperature was 37° C. $IC_{50}$ values were determined for compounds showing an inhibitory effect on SCCE activity at concentrations of 10 µM or lower. The IC50 values were used to identify compounds as SCCE inhibitors of the invention.

Results

TABLE 1A

| Compound | | IC$_{50}$ μM |
|---|---|---|
| I-1 | 2-Phenyl-benzo[d][1,3]oxazin-4-one | 2 |
| I-2 | 7-Chloro-2-(2-chloro-4-nitro-phenyl)-benzo[d][1,3]oxazin-4-one | 0.1 |
| I-3 | 2-(2-Iodo-phenyl)-6,7-dimethoxy-benzo[d][1,3]oxazin-4-one | 0.1 |
| I-4 | 7-Chloro-2-thiophen-2-yl-benzo[d][1,3]oxazin-4-one | 0.25 |
| I-5 | 2-(2-Chloro-4-nitro-phenyl)-6,7-dimethoxy-benzo[d][1,3]oxazin-4-one | 0.5 |
| I-6 | 2-(2-Chloro-5-nitro-phenyl)-benzo[d][1,3]oxazin-4-one | 0.5 |
| I-7 | 5,7-Dichloro-2-(dimethylamino-benz[d][1,3]oxazin-4-one | 2 |
| I-8 | 2-Pyridin-4-yl-benzo[d][1,3]oxazin-4-one | 5 |
| I-9 | 2-Thiophen-2-yl-benzo[d][1,3]oxazin-4-one | 5 |
| I-10 | 2-(2-Hydroxy-phenyl)-benzo[d][1,3]oxazin-4-one | 5 |
| I-11 | 2-(2-Fluoro-phenyl)-6,7-dimethoxy-benzo[d][1,3]oxazin-4-one | 0.7 |
| I-12 | 7-Chloro-2-(4-ethyl-phenyl)benzo[d][1,3]oxazin-4-one | 2 |
| I-13 | 7-Chloro-2-(3-methyl-4-nitro-phenyl)-benzo[d][1,3]oxazin-4-one | 2 |
| I-14 | N-[4-(6,7-Dimethoxy-4-oxo-4H-benzo[d][1,3]oxazin-2-yl)-phenyl]-acetamide | 5 |
| I-15 | Acetic acid 4-(4-oxo-4H-benzo[d][1,3]oxazin-2-yl)-phenyl ester | 5 |
| I-16 | 2-(2-Chloro-phenyl)-6,7-dimethoxy-benzo[d][1,3]oxazin-4-one | 0.17 |
| I-17 | 6-Chloro-2-thiophen-2-yl-benzo[e][1,3]oxazin-4-one | 0.32 |
| I-18 | 6-Chloro-2-furan-2-yl-benzo[e][1,3]oxazin-4-one | 0.60 |
| I-19 | 2-(2-Chlorophenyl)-benzo[e][1,3]oxazin-4-one | 4 |
| II-1 | 6-Ethyl-2-(2-fluoro-phenyl)-thieno[2,3-d][1,3]oxazin-4-one | 0.07 |
| II-2 | 6-Methyl-2-naphtalen-1-yl-thieno[2,3-d][1,3]oxazin-4-one | 0.05 |
| II-3 | 6-Ethyl-2-o-tolyl-thieno[2,3-d][1,3]oxazin-4-one | 0.15 |
| II-4 | 6-Ethyl-2-(4-fluoro-phenyl)-thieno[2,3-d][1,3]oxazin-4-one | 0.3 |
| II-5 | 2-(2-chloro-phenyl)-4H-thieno[3,2-d][1,3]oxazin-4-one | 0.5 |
| II-6 | 2-phenyl-4H-thieno[3,2-d][1,3]oxazin-4-one | 1 |
| II-7 | 2-Furan-2-yl-5,6-dimethyl-thieno[2,3-d][1,3]oxazin-4-one | 1.5 |
| II-8 | 2-(4-fluoro-phenyl)-4H-thieno[3,2-d][1,3]oxazin-4-one | 1 |
| II-9 | 2-(4-Bromo-phenyl)-6-ethyl-thieno[2,3-d][1,3]oxazin-4-one | 1 |
| II-10 | 6-(2-Chloro-phenyl)-2,3-dihydro-1H-5-oxa-8-thia-7-aza-cyclopenta[a]inden-4-one | 0.02 |
| II-11 | 6-Furan-2-yl-2,3-dihydro-1H-5-oxa-8-thia-7-aza-cyclopenta[a]inden-4-one | 0.2 |
| II-12 | 6-Phenyl-2,3-dihydro-1H-5-oxa-8-thia-7-aza-cyclopenta[a]inden-4-one | 0.2 |
| II-13 | 6-(4-Fluoro-phenyl)-2,3-dihydro-1H-5-oxa-8-thia-7-aza-cyclopenta[a]inden-4-one | 0.3 |
| II-14 | 6-Thiophen-2-yl-2,3-dihydro-1H-5-oxo-8-thia-7-aza-cyclopenta[a]inden-4-one | 0.3 |
| II-15 | 2-(2-Fluoro-phenyl)-5,6,7,8-tetrahydro-3-oxa-9-thia-1-aza-fluoren-4-one | 0.07 |
| II-16 | 2-(2-Methoxy-phenyl)-5,6,7,8-tetrahydro-3-oxa-9-thia-1-aza-fluoren-4-one | 0.07 |
| II-17 | 2-Phenyl-5,6,7,8-tetrahydro-3-oxa-9-thia-1-aza-fluoren-4-one | 0.7 |
| II-18 | 2-Naphtalen-1-yl-5,6,7,8-tetrahydro-3-oxa-9-thia-1-aza-fluoren-4-one | 1 |
| II-19 | 2-Thiophen-2-yl-5,6,7,8-tetrahydro-3-oxa-9-thia-1-aza-fluoren-4one | 1 |
| II-20 | 2-(3-Methoxy-phenyl)-5,6,7,8-tetrahydro-3-oxa-9-thia-1-aza-fluoren-4-one | 2 |
| II-21 | 2-Pyridin-4-yl-6,7,8,9-tetrahydro-5H-3-oxa-10-thia-1-aza-benzo[a]azulen-4-one | 2 |
| II-22 | 2-Methyl-6,7,8,9-tetrahydro-5H-3-oxa-10-thia-1-aza-benzo[a]azulen-4-one | >10 |

TABLE 1B

| | % SCCE activity | | |
|---|---|---|---|
| Compound | 1 μM | 5 μM | 10 μM |
| I-1 | | | 27 |
| I-2 | 15 | 0 | |
| I-3 | | | 0 |
| I-4 | 22 | 5 | |
| I-5 | | | 9 |
| I-6 | | | 22 |
| I-7 | | | 7 |
| I-8 | | | 24 |
| I-9 | | | 23 |
| I-10 | 71 | 47 | 32 |
| I-11 | 39 | 8 | |
| I-12 | 33 | 15 | |
| I-13 | 56 | 36 | |
| I-14 | | | 52 |
| I-15 | 52 | 22 | |
| I-16 | 15 | | 3 |
| I-17 | 18 | 4 | |
| I-18 | 26 | 7 | |
| I-19 | 76 | 44 | |
| I-20 | 54 | 16 | |
| I-21 | 47 | 16 | |
| II-1 | 0 | 0 | |
| II-2 | | 4 | |
| II-3 | 3 | 0 | |
| II-4 | 15 | 8 | |
| II-5 | | | 1 |
| II-6 | | | 9 |
| II-7 | 50 | 13 | |
| II-8 | | | 10 |
| II-9 | 58 | 37 | |
| II-10 | 10 | 2 | |
| II-11 | 8 | 8 | |
| II-12 | 19 | 16 | |
| II-13 | 37 | 14 | |
| II-14 | 37 | 21 | |
| II-15 | 7 | 2.4 | |
| II-16 | 2.7 | 0 | |
| II-17 | 45 | 33 | |
| II-18 | 38 | 41 | |
| II-19 | 52 | 41 | |
| II-20 | 52 | 42 | |
| II-22 | 49 | 27 | |
| II-23 | 68 | 25 | |

Example 2

In Vivo Evaluation of Compounds

Animal Model

Transgenic mice over-expressing human SCCE under the control of the SV40 early promoter were generated as described in WO 02/062135. These transgenic mice show a pattern of SCCE-expression which is similar to the expression pattern seen in psoriasis lesions and chronic lesions in atopic dermatitis in humans, i.e. expression in suprabasal cells which increases with distance from the basal layer. The transgenic mice develop pathological skin changes with marked hyperkeratosis, increased epidermal thickness, and dermal inflammation. From the age of 8-10 weeks transgenic mice show signs of itch, the frequency of which increase with age. The increase marked changes in skin morphology including increased epidermal thickness, also causes higher transepidermal water loss.

In Vivo Effect of SCCE Inhibitors

Transgenic mice, 6-9 month of age, were treated daily with compound I-3 (2-(2-Iodo-phenyl)-6,7-dimethoxy-benzo[d][1,3]oxazin-4-one) which was identified as an SCCE inhibitor as described above during 8 days. The substance was initially dissolved in DMSO and formulated in vehicle containing 45% isopropanol, 6% 1,2-propanediol with a 1.2% final concentration of DMSO. Two different concentrations of inhibitor, 300 μM and 30 μM, were formulated.

The study contained four different treatments with 3-4 mice in each group. Each mouse used in the study had phenotypic changes typical of SCCE transgenic animals.

Treatments:
- high dose (300 μM) of compound I-3
- low dose (30 μM) of compound I-3
- positive control (a pharmaceutical formulation (Betnovat, Glaxo SmithKline AB) containing betametasone)
- negative control, vehicle (a pharmaceutical formulation lacking active substance)

The formulations (500 μl/mouse) were applied once daily (late afternoon) on the area around the ears and on the back of the mice. Mice were treated during 8 days and measurements of transepidermal water loss (TEWL) were performed during the treatment period.

Transepidermal Water Loss (TEWL)

TEWL was measured on the back of mice with an Evaporimeter from DermaLAB (Cortex Technology ApS, Hadsund, Denmark) according to manufactures protocol. Before measurements, mice were given an intraperitoneal injection of Dormicum, Hypnorm and sterile water as cocktail (1:1:2). The dose used, 2.5 μl per gram body weight. TEWL was measured on in the morning at day 0, 3, 5 and 8 for 1 min repeated twice.

Results—TEWL

Both concentrations of inhibitor improves TEWL with approximately half the efficiency of the positive control (Betamethasone) see FIG. 1.

Histological Changes

Histological studies of skin morphology were performed on sacrificed mice after the last day of treatment (day 8). Tissue samples were fixed in 4% phosphate-buffered formaldehyde for 24 h in room temperature (RT) and then embedded in paraffin using standard histological procedure. To analyze tissue morphology, embedded tissue was sectioned (5 μm) and then stained with haematoxylin and Eosin (H/E) using standard histological protocols.

Results—Histological Changes

Both concentrations of inhibitor had positive effects on skin morphology to a higher degree then vehicle group, without the side effects (unusually thin epidermis) found in the positive control group (Betamethasone) see Table 2.

TABLE 2

Skin morphology after treatment

| Treatment | Morphology changes | Unusually thin epidermis |
|---|---|---|
| Vehicle | 2/4 | 0/4 |
| Betamethasone | 0/3 | 3/3 |
| Compound I-3, 30 μM | 1/4 | 0/4 |
| Compound I-3, 300 μM | 1/4 | 0/4 |

The invention claimed is:

1. A method for treatment of a skin disease in a mammal, wherein the skin disease is selected from the group consisting of atopic dermatitis, contact dermatitis, eczema, psoriasis, acne, epidermal hyperkeratosis, acanthosis, epidermal inflammation, dermal inflammation and pruritus, and wherein the mammal has symptoms of the skin disease and the treatment reduces the symptoms wherein the method comprises topically administering to the mammal an effective amount of at least one compound with formula I or II:

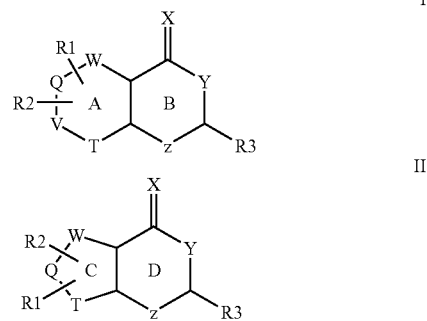

wherein

X is O or S; Y is independently O, S, NH or N if the nitrogen atom is bonded to an adjacent carbon atom via a double bond; Z is independently O, NH or N if the nitrogen atom is bonded to an adjacent carbon atom via a double bond;

W, Q, V, and T are independently CH, $CH_2$, S, N, or O;

ring A, ring B, ring C and ring D may be aromatic, saturated or partly saturated;

$R_1$ and $R_2$ are optional substitutents independently selected from $C_{1-8}$-alkyl, $C_{2-8}$-alkenyl, $C_{2-8}$-alkynyl or $C_{3-6}$-cycloalkyl, each optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$, H, halogen, $CF_3$, $C_{1-6}$-alkoxy, $C_{1-6}$alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$alkoxycarbonyl, aryl, aryloxy, heteroaryl, heteroaryloxy, alkylphenyl, or tetrazole;

or $R_1$ and $R_2$, when bonded to adjacent atoms in ring A or ring C, optionally together form a moiety —$(CH_2)_n$—, where n=1-5, and wherein 1, 2 or 3 $CH_2$ units in said moiety are optionally replaced by 1, 2 or 3 heteroatoms, wherein each heteroatom is individually selected from the group consisting of O, S, NH and N if the nitrogen atom is bonded to an adjacent atom via a double bond, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$ alkoxy, trifluoromethoxy, carbamoyl, $CONHR_4$, or $CON(R_4)_2$;

$R_3$ is aryl or heteroaryl, each optionally substituted with one or more halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, tetrazole, $C_{1-8}$-alkyl, $C_{2-8}$-alkenyl, $C_{2-8}$-alkynyl or $C_{3-6}$-cycloalkyl, each $C_{1-8}$-alkyl, $C_{2-8}$-alkenyl, $C_{2-8}$-alkynyl or $C_{3-6}$-cycloalkyl being optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl; and $R_4$ is $C_{1-4}$-alkyl, $C_{2-4}$-alkenyl, $C_{2-4}$-alkynyl, $C_{3-6}$-cycloalkyl, $C_{1-6}$-alkylthio, aryl, aryloxy, heteroaryl, or heteroaryloxy;

or a pharmaceutical acceptable salt thereof.

2. The method according to claim 1, wherein said skin disease is selected from the group consisting of atopic dermatitis, contact dermatitis, eczema, psoriasis, acne, epidermal hyperkeratosis, acanthosis, and pruritus.

3. A method for treatment of a skin disease in a mammal, wherein said skin disease is selected from the group consisting of psoriasis and pruritus, which method comprises topically administering to the mammal an effective amount of at least one compound with formula I or II:

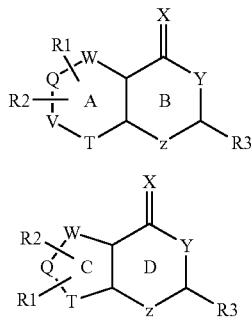

wherein

X is O or S; Y is independently O, S, NH or N if the nitrogen atom is bonded to an adjacent carbon atom via a double bond; Z is independently O, NH or N if the nitrogen atom is bonded to an adjacent carbon atom via a double bond;

W, Q, V, and T are independently CH, $CH_2$, S, N, or O;

ring A, ring B, ring C and ring D may be aromatic, saturated or partly saturated;

$R_1$ and $R_2$ are optional substituents independently selected from $C_{1-8}$-alkyl, $C_{2-8}$-alkenyl, $C_{2-8}$-alkynyl or $C_{3-6}$-cycloalkyl, each optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; H, halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, or tetrazole;

or $R_1$ and $R_2$, when bonded to adjacent atoms in ring A or ring C, optionally together form a moiety $—(CH_2)_n—$, where n=1-5, and wherein 1, 2 or 3 $CH_2$ units in said moiety are optionally replaced by 1, 2 or 3 heteroatoms, wherein each heteroatom is individually selected from the group consisting of O, S, NH and N if the nitrogen atom is bonded to an adjacent atom via a double bond, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$ alkoxy, trifluoromethoxy, carbamoyl, $CONHR_4$, or $CON(R_4)_2$;

$R_3$ is aryl or heteroaryl each optionally substituted with one or more halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, tetrazole, $C_{1-8}$-alkyl, $C_{2-8}$-alkenyl, $C_{2-8}$-alkynyl or $C_{3-6}$-cycloalkyl, each $C_{1-8}$-alkyl, $C_{2-8}$-alkenyl, $C_{2-8}$-alkynyl or $C_{3-6}$-cycloalkyl being optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl; and $R_4$ is $C_{1-4}$-alkyl, $C_{2-4}$-alkenyl, $C_{2-4}$-alkynyl, $C_{3-6}$-cycloalkyl, $C_{1-6}$-alkoxy, $C_{1-6}$-alkylthio, aryl, aryloxy, heteroaryl, or heteroaryloxy;

or a pharmaceutical acceptable salt thereof.

4. The method according to claim 1, wherein the compound is selected from compounds of formula Ia and IIa

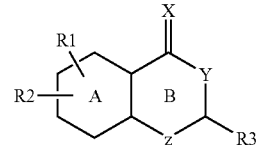

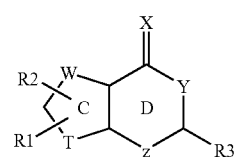

wherein

X is O or S; Y is independently O, S, NH or N if the nitrogen atom is bonded to an adjacent carbon atom via a double bond; Z is independently O, NH or N if the nitrogen atom is bonded to an adjacent carbon atom via a double bond;

T and W are CH, $CH_2$, or S, wherein one of T and W is S;

ring A, ring B, ring C and ring D may be aromatic, saturated or partly saturated; and $R_1$, $R_2$ and $R_3$ are as defined in claim 1.

5. The method according to claim 4, wherein X is O; Y is independently O, NH or N if the nitrogen atom is bonded to an adjacent carbon atom via a double bond; Z is independently O, NH or N if the nitrogen atom is bonded to an adjacent carbon atom via a double bond.

6. The method according to claim 5, wherein ring A and ring C are aromatic and wherein ring B and ring D are partly saturated.

7. The method according to claim 6, wherein the compound is selected from compounds having the below listed formulas:

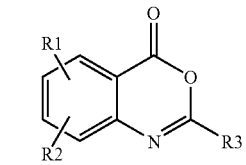 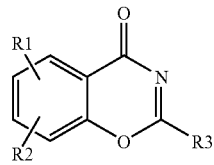

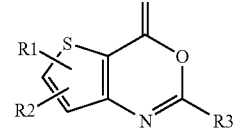 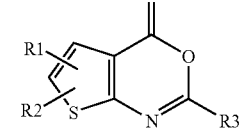

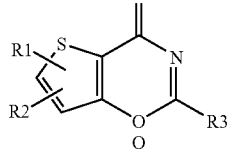 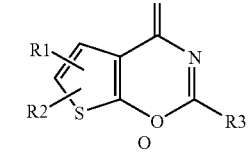

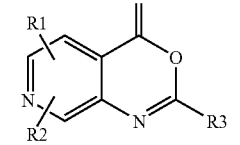 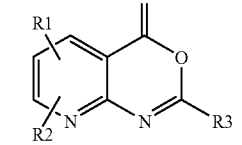

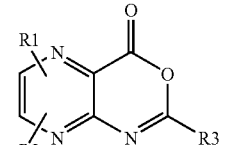 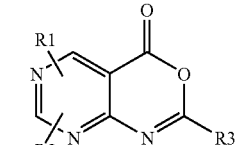

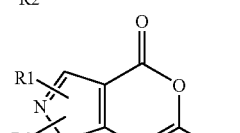 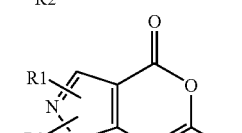

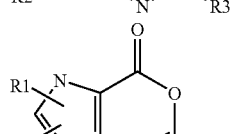 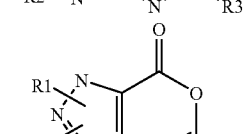

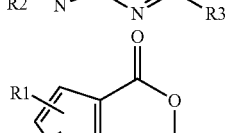 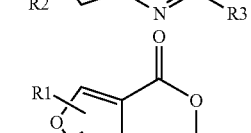

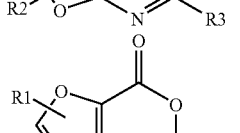 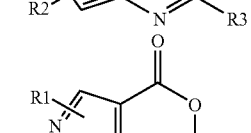

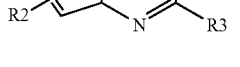

wherein $R_1$, $R_2$ and $R_3$ are as defined in claim 1.

8. The method according to claim 7, wherein $R_1$ and $R_2$, if present, are independently $C_{1-8}$-alkyl optionally substituted with halogen, OH, $NH_2$, $NHR_4$, $N(R_4)_2$, $NHCOR_4$, $C_{1-6}$-alkoxy, trifluoromethoxy, carbamoyl, $CONHR_4$ or $CON(R_4)_2$; halogen, $C_{1-6}$-alkoxy;

or $R_1$ and $R_2$, when bonded to adjacent atoms, optionally together form a moiety —$(CH_2)_n$—, where n=3, 4 or 5, and wherein said moiety may optionally be substituted with 1, 2 or 3 substituents individually selected from the group consisting of halogen, OH, $NH_2$, $NHR_4$, $N(R_4)_2$, $NHCOR_4$, $C_{1-6}$-alkoxy, trifluoromethoxy, carbamoyl, $CONHR_4$, or $CON(R_4)_2$.

9. The method according to claim 8, wherein $R_1$ and $R_2$, if present, are independently chlorine or O—$CH_3$.

10. The method according to claim 8, wherein the compound is selected from compounds having the below listed formulas:

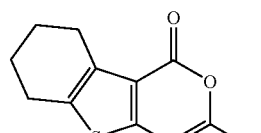

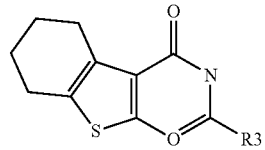

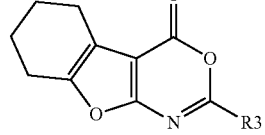

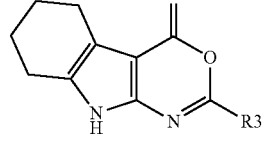

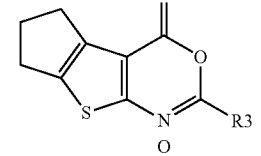

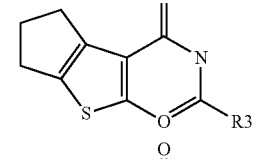

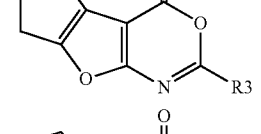

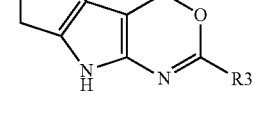

-continued

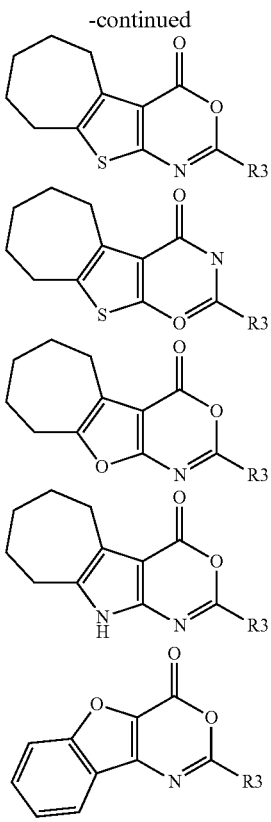

wherein R₃ is as defined in claim 1.

11. The method according to claim 1, wherein R₃ is phenyl, 1-naphthyl, 4-pyridinyl, 2-furanyl or 2-thienyl, each optionally substituted with halogen, $CF_3$, $OCF_3$, COOH, CN, $CONH_2$, $CONHR_4$, $CON(R_4)_2$, OH, $NO_2$, $NH_2$, $NHR_4$, $N(R_4)_2$, $NHCOR_4$, $NHSO_2R_4$, $SO_2NH_2$, $SO_2NHR_4$, $SO_2R_4$, $SOR_4$, $C_{1-4}$ alkoxy, or carbamoyl; halogen, $CF_3$, $C_{1-6}$-alkoxy, $C_{1-6}$-alkylthio, $OCF_3$, COOH, CN, $CONH_2$, $CONHR_4$, OH, $NO_2$, $NH_2$, $NHR_4$, $N(R_4)_2$, $NHCOR_4$, $NHSO_2R_4$, $CON(R_4)_2$, $CONHSO_2R_4$, $SO_2NH_2$, $SO_2NHR_4$, $SO_2R_4$, $SOR_4$, $C_{1-4}$-alkoxycarbonyl, aryl, aryloxy, heteroaryl, heteroaryloxy, alkylphenyl, or tetrazole.

12. The method according to claim 1, wherein the compound is selected from the group consisting of
2-Phenyl-benzo[d][1,3]oxazin-4-one,
7-Chloro-2-(2-chloro-4-nitro-phenyl)benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
5,7-Dichloro-2-(dimethylamino-benz[d][1,3]oxazin-4-one,
2-Pyridin-4-yl-benzo[d][1,3]oxazin-4-one,
2-Thiophen-2-yl-benzo[d][1,3]oxazin-4-one,
2-(2-Hydroxy-phenyl)-benzo[d][1,3]oxazin-4-one,
2-(2-Fluoro-phenyl)-6,7-dimethoxy-benzo[d][1,3]oxazin-4-one,
7-Chloro-2-(4-ethyl-phenyl)benzo[d][1,3]oxazin-4-one,
7-Chloro-2-(3-methyl-4-nitro-phenyl)-benzo[d][1,3]oxazin-4-one,
N-[4-(6,7-Dimethoxy-4-oxo-4H-benzo[d][1,3]oxazin-2-yl)-phenyl]-acetamide,
Acetic acid 4-(4-oxo-4H-benzo[d][1,3]oxazin-2-yl)-phenyl ester,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
2-(2-Chlorophenyl)-benzo[e][1,3]oxazin-4-one,
2-Thiophen-2-yl-benzo[e][1,3]oxazin-4-one,
2-Furan-2-yl-benzo[e][1,3]oxazin-4-one,
6-Ethyl-2-(2-fluoro-phenyl)-thieno[2,3-d][1,3]oxazin-4-one,
6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
2-phenyl-4H-thieno[3,2-d][1,3]oxazin-4-one,
2-Furan-2-yl-5,6-dimethyl-thieno[2,3-d][1,3]oxazin-4-one,
2-(4-fluoro-phenyl)-4H-thieno[3,2-d][1,3]oxazin-4-one,
2-(4-Bromo-phenyl)-6-ethyl-thieno[2,3-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Phenyl-5,6,7,8-tetrahydro-3-oxa-9-thia-1-aza-fluoren-4-one,
2-Naphthalen-1-yl-5,6,7,8-tetrahydro-3-oxa-9-thia-1-aza-fluoren-4-one,
2-Thiophen-2-yl-5,6,7,8-tetrahydro-3-oxa-9-thia-1-aza-fluoren-4-one,
2-(3-Methoxy-phenyl)-5,6,7,8-tetrahydro-3-oxa-9-thia-1-aza-fluoren-4-one,
2-Pyridin-4-yl-6,7,8,9-tetrahydro-5H-3-oxa-10-thia-1-aza-benzo[a]azulen-4-one,
and pharmaceutical acceptable salts thereof.

13. The method according to claim 12, wherein the compound is selected from the group consisting of
7-Chloro-2-(2-chloro-4-nitro-phenyl)-benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
2-(2-Fluoro-phenyl)-6,7-dimethoxy-benzo[d][1,3]oxazin-4-one,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
6-Ethyl-2-(2-fluoro-phenyl)-thieno[2,3-d][1,3]oxazin-4-one, 6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Phenyl-5,6,7,8-tetrahydro-3-oxa-9-thia-1-aza-fluoren-4-one,
and pharmaceutical acceptable salts thereof.

14. The method according to claim 2, wherein the compound is selected from the group consisting of
2-Phenyl-benzo[d][1,3]oxazin-4-one,
7-Chloro-2-(2-chloro-4-nitro-phenyl)-benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
5,7-Dichloro-2-(dimethylamino-benz[d][1,3]oxazin-4-one,
2-Pyridin-4-yl-benzo[d][1,3]oxazin-4-one,
2-Thiophen-2-yl-benzo[d][1,3]oxazin-4-one,
2-(2-Hydroxy-phenyl)-benzo[d][1,3]oxazin-4-one,
2-(2-Fluoro-phenyl)-6,7-dimethoxy-benzo[d][1,3]oxazin-4-one,
7-Chloro-2-(4-ethyl-phenyl)benzo[d][1,3]oxazin-4-one,
7-Chloro-2-(3-methyl-4-nitro-phenyl)benzo[d][1,3]oxazin-4-one,
N-[4-(6,7-Dimethoxy-4-oxo-4H-benzo[d][1,3]oxazin-2-yl)-phenyl]-acetamide,
Acetic acid 4-(4-oxo-4H-benzo[d][1,3]oxazin-2-yl)-phenyl ester,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
2-(2-Chlorophenyl)-benzo[e][1,3]oxazin-4-one,
2-Thiophen-2-yl-benzo[e][1,3]oxazin-4-one,
2-Furan-2-yl-benzo[e][1,3]oxazin-4-one,
6-Ethyl-2-(2-fluoro-phenyl)-thieno[2,3-d][1,3]oxazin-4-one,
6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
2-phenyl-4H-thieno[3,2-d][1,3]oxazin-4-one,
2-Furan-2-yl-5,6-dimethyl-thieno[2,3-d][1,3]oxazin-4-one,
2-(4-fluoro-phenyl)-4H-thieno[3,2-d][1,3]oxazin-4-one,
2-(4-Bromo-phenyl)-6-ethyl-thieno[2,3-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Phenyl-5,6,7,8-tetrahydro-3-oxa-9-thia-1-aza-fluoren-4-one,
2-Naphthalen-1-yl-5,6,7,8-tetrahydro-3-oxa-9-thia-1-aza-fluoren-4-one,
2-Thiophen-2-yl-5,6,7,8-tetrahydro-3-oxa-9-thia-1-aza-fluoren-4-one,
2-(3-Methoxy-phenyl)-5,6,7,8-tetrahydro-3-oxa-9-thia-1-aza-fluoren-4-one,
2-Pyridin-4-yl-6,7,8,9-tetrahydro-5H-3-oxa-10-thia-1-aza-benzo[a]azulen-4-one,
and pharmaceutical acceptable salts thereof.

15. The method according to claim 14, wherein the compound is selected from the group consisting of
7-Chloro-2-(2-chloro-4-nitro-phenyl)-benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
2-(2-Fluoro-phenyl)-6,7-dimethoxy-benzo[d][1,3]oxazin-4-one,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
6-Ethyl-2-(2-fluoro-phenyl)-thieno[2,3-d][1,3]oxazin-4-one,
6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one, 2-Phenyl-5,6,7,8-tetrahydro-3-oxa-9-thia-1-aza-fluoren-4-one, and pharmaceutical acceptable salts thereof.

16. The method according to claim 3, wherein the compound is selected from the group consisting of 2-Phenyl-benzo[d][1,3]oxazin-4-one,
7-Chloro-2-(2-chloro-4-nitro-phenyl)-benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
5,7-Dichloro-2-(dimethylamino-benz[d][1,3]oxazin-4-one,
2-Pyridin-4-yl-benzo[d][1,3]oxazin-4-one,
2-Thiophen-2-yl-benzo[d][1,3]oxazin-4-one,
2-(2-Hydroxy-phenyl)-benzo[d][1,3]oxazin-4-one,
2-(2-Fluoro-phenyl)-6,7-dimethoxy-benzo[d][1,3]oxazin-4-one,
7-Chloro-2-(4-ethyl-phenyl)benzo[d][1,3]oxazin-4-one,
7-Chloro-2-(3-methyl-4-nitro-phenyl)-benzo[d][1,3]oxazin-4-one,
N-[4-(6,7-Dimethoxy-4-oxo-4H-benzo[d][1,3]oxazin-2-yl)-phenyl]-acetamide,
Acetic acid 4-(4-oxo-4H-benzo[d][1,3]oxazin-2-yl)-phenyl ester,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
2-(2-Chlorophenyl)-benzo[e][1,3]oxazin-4-one,
2-Thiophen-2-yl-benzo[e][1,3]oxazin-4-one,
2-Furan-2-yl-benzo[e][1,3]oxazin-4-one,
6-Ethyl-2-(2-fluoro-phenyl)-thieno[2,3-d][1,3]oxazin-4-one,
6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
2-phenyl-4H-thieno[3,2-d][1,3]oxazin-4-one,
2-Furan-2-yl-5,6-dimethyl-thieno[2,3-d][1,3]oxazin-4-one,
2-(4-fluoro-phenyl)-4H-thieno[3,2-d][1,3]oxazin-4-one,
2-(4-Bromo-phenyl)-6-ethyl-thieno[2,3-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Phenyl-5,6,7,8-tetrahydro-3-oxa-9-thia-1-aza-fluoren-4-one,
2-Naphthalen-1-yl-5,6,7,8-tetrahydro-3-oxa-9-thia-1-aza-fluoren-4-one,
2-Thiophen-2-yl-5,6,7,8-tetrahydro-3-oxa-9-thia-1-aza-fluoren-4-one,
2-(3-Methoxy-phenyl)-5,6,7,8-tetrahydro-3-oxa-9-thia-1-aza-fluoren-4-one,
2-Pyridin-4-yl-6,7,8,9-tetrahydro-5H-3-oxa-10-thia-1-aza-benzo[a]azulen-4-one, and pharmaceutical acceptable salts thereof.

17. The method according to claim 16, wherein the compound is selected from the group consisting of 7-Chloro-2-(2-chloro-4-nitro-phenyl)-benzo[d][1,3]oxazin-4-one,
2-(2-Iodo-phenyl)-6,7-dimethoxy-benzo[d][1,3]oxazin-4-one,
7-Chloro-2-thiophen-2-yl-benzo[d][1,3]oxazin-4-one,
2-(2-Chloro-4-nitro-phenyl)-6,7-dimethoxy-benzo[d][1,3]oxazin-4-one,
2-(2-Chloro-5-nitro-phenyl)-benzo[d][1,3]oxazin-4-one,
2-(2-Fluoro-phenyl)-6,7-dimethoxy-benzo[d][1,3]oxazin-4-one,
2-(2-Chlorophenyl)-6,7-dimethoxy-benzo[d][1,3]oxazin-4-one,
6-Chloro-2-thiophen-2-yl-benzo[e][1,3]oxazin-4-one,
6-Chloro-2-furan-2-yl-benzo[e][1,3]oxazin-4-one,
6-Ethyl-2-(2-fluoro-phenyl)-thieno[2,3-d][1,3]oxazin-4-one,
6-Methyl-2-naphthalen-1-yl-thieno[2,3-d][1,3]oxazin-4-one,
6-Ethyl-2-o-tolyl-thieno[2,3-d][1,3]oxazin-4-one,
6-Ethyl-2-(4-fluoro-phenyl)-thieno[2,3-d][1,3]oxazin-4-one,
2-(2-chloro-phenyl)-4H-thieno[3,2-d][1,3]oxazin-4-one,
6-(2-Chloro-phenyl)-2,3-dihydro-1H-5-oxa-8-thia-7-aza-cyclopenta[a]indene-4-one,
6-Furan-2-yl-2,3-dihydro-1H-5-oxa-8-thia-7-aza-cyclopenta[a]inden-4-one,
6-Phenyl-2,3-dihydro-1H-5-oxa-8-thia-7-aza-cyclopenta[a]inden-4-one,
6-(4-Fluoro-phenyl)-2,3-dihydro-1H-5-oxa-8-thia-7-aza-cyclopenta[a]inden-4-one,
6-Thiophen-2-yl-2,3-dihydro-1H-5-oxo-8-thia-7-aza-cyclopenta[a]inden-4-one,
2-(2-Fluoro-phenyl)-5,6,7,8-tetrahydro-3-oxa-9-thia-1-aza-fluoren-4-one,
2-(2-Methoxy-phenyl)-5,6,7,8-tetrahydro-3-oxa-9-thia-1-aza-fluoren-4-one,
2-Phenyl-5,6,7,8-tetrahydro-3-oxa-9-thia-1-aza-fluoren-4-one, and pharmaceutical acceptable salts thereof.

18. The method according to claim 1, wherein said skin disease is atopic dermatitis, contact dermatitis or psoriasis.

19. The method according to claim 1, wherein said skin disease is acne, epidermal hyperkeratosis or acanthosis.

20. The method according to claim 1, wherein said skin disease is eczema, epidermal inflammation or dermal inflammation.

21. The method according to claim 1, wherein said skin disease is psoriasis or pruritus.

22. The method according to claim 21, wherein said skin disease is pruritus.

23. The method according to claim 21, wherein said skin disease is psoriasis.

24. The method according to claim 3, wherein said compound is 2-(2-iodophenyl)-6,7-dimethoxybenzo[d][1,3]oxazin-4-one.

* * * * *

UNITED STATES PATENT AND TRADEMARK OFFICE
CERTIFICATE OF CORRECTION

| | | |
|---|---|---|
| PATENT NO. | : 7,872,052 B2 | Page 1 of 1 |
| APPLICATION NO. | : 10/559322 | |
| DATED | : January 18, 2011 | |
| INVENTOR(S) | : Marcel Linschoten | |

It is certified that error appears in the above-identified patent and that said Letters Patent is hereby corrected as shown below:

Col. 38, Line 55, Claim 1, delete "substitutents" and insert -- substituents --.

Col. 38, Line 59, Claim 1, delete "$CON(R_4)_2$," and insert -- $CON(R_4)_2$; --.

Col. 38, Line 60, Claim 1, delete "$C_{1-6}$alkylthio," and insert -- $C_{1-6}$-alkylthio --.

Col. 38, Line 64, Claim 1, delete "$C_{1-4}$alkoxycarbonyl" and insert -- $C_{1-4}$-alkoxycarbonyl --.

Col. 39, Line 7, Claim 1, delete "substitutents" and insert -- substituents --.

Col. 39, Line 9, Claim 1, delete "$C_{1-6}$ alkoxy" and insert -- $C_{1-6}$-alkoxy --.

Col. 39, Line 23, Claim 1, delete "$C_{1-4}$ alkoxy" and insert -- $C_{1-4}$-alkoxy --.

Col. 40, Line 17, Claim 3, delete "$C_{1-6}$ alkoxy" and insert -- $C_{1-6}$-alkoxy --.

Col. 40, Line 19, Claim 3, delete "heteroaryl" and insert -- heteroaryl, --.

Col. 40, Line 31, Claim 3, delete "$C_{1-4}$ alkoxy" and insert -- $C_{1-4}$-alkoxy --.

Col. 43, Line 48, Claim 12, delete "phenyl)benzo" and insert -- phenyl)-benzo --.

Col. 43, Line 63, Claim 12, delete "phenyl)benzo" and insert -- phenyl)-benzo --.

Col. 45, Line 42, Claim 14, delete "phenyl)benzo" and insert -- phenyl)-benzo --.

Col. 45, Line 43, Claim 14, delete "phenyl)benzo" and insert -- phenyl)-benzo --.

Col. 47, Line 22, Claim 16, delete "phenyl)benzo" and insert -- phenyl)-benzo --.

Signed and Sealed this
Eleventh Day of September, 2012

David J. Kappos
*Director of the United States Patent and Trademark Office*